United States Patent
Vu et al.

(10) Patent No.: US 10,083,341 B2
(45) Date of Patent: Sep. 25, 2018

(54) CELLULAR ACTIVITY QUANTIFICATION USING LABELED PROBES

(71) Applicants: Tania Vu, Portland, OR (US); Thomas Jacob, Beaverton, OR (US)

(72) Inventors: Tania Vu, Portland, OR (US); Thomas Jacob, Beaverton, OR (US)

(73) Assignee: Oregon Health & Science University, Portland, OR (US)

( * ) Notice: Subject to any disclaimer, the term of this patent is extended or adjusted under 35 U.S.C. 154(b) by 3 days.

(21) Appl. No.: 14/946,535

(22) Filed: Nov. 19, 2015

(65) Prior Publication Data

US 2016/0140382 A1     May 19, 2016

Related U.S. Application Data

(60) Provisional application No. 62/081,926, filed on Nov. 19, 2014.

(51) Int. Cl.
| | | |
|---|---|---|
| *G06K 9/00* | (2006.01) | |
| *G01N 33/50* | (2006.01) | |
| *G06T 7/00* | (2017.01) | |

(52) U.S. Cl.
CPC ..... *G06K 9/00147* (2013.01); *G01N 33/5011* (2013.01); *G06K 9/0014* (2013.01); *G06T 7/0014* (2013.01); *G06T 2207/10064* (2013.01); *G06T 2207/20076* (2013.01); *G06T 2207/30072* (2013.01)

(58) Field of Classification Search
CPC ............ G06K 9/00147; G06K 9/0014; G06K 9/00127; G06T 7/0014; G06T 2207/20076; G06T 2207/10064; G06T 2207/30072; G01N 33/5011
See application file for complete search history.

(56) References Cited

U.S. PATENT DOCUMENTS

| 7,052,915 B2 | 5/2006 | Aebersold et al. |
| 7,799,526 B2 | 7/2010 | Howe |
| (Continued) | | |

FOREIGN PATENT DOCUMENTS

| WO | 2008051985 A2 | 5/2008 |
| WO | 2010127114 A2 | 11/2010 |

OTHER PUBLICATIONS

Hatakeyama et al. "Development of Dual-Color Simultaneous Single Molecule Imaging System for Analyzing Multiple Intracellular Trafficking Activities." 35th Annual International Conference of the IEEE EMBS, Jul. 3, 2013, pp. 1418-1421.*

(Continued)

*Primary Examiner* — Jon Chang

(57) ABSTRACT

Methods and systems for quantifying cellular activity using labeled probes, e.g., quantum dots, are disclosed. In one example approach, a method for quantifying cellular activity in a sample containing intact cells having labeled complexes comprises receiving images of the sample at a plurality of depths and detecting individual intact cells in the images of the sample at the plurality of depths. For each detected cell, discrete labels may be detected and localized in the cell at each depth, a total number of detected and localized labels may be calculated in the cell, and an activity level of the target molecule for the labeled probe in the cell determined.

19 Claims, 18 Drawing Sheets

(56) References Cited

U.S. PATENT DOCUMENTS

| | | | |
|---|---|---|---|
| 7,767,421 B2* | 8/2010 | Gee | C12Q 1/68 435/91.1 |
| 2001/0041347 A1* | 11/2001 | Sammak | G01N 33/5005 435/7.23 |
| 2014/0212890 A1 | 7/2014 | Vu et al. | |

OTHER PUBLICATIONS

Ram et al. "Localizing Single Molecules in Three Dimensions—A Brief Review." 42nd Asilomar Conference on Signals, Systems and Computers, Oct. 26, 2008, pp. 64-66.*

Delom, F. & Chevet, E. Phosphoprotein analysis: from proteins to proteomes. Proteome Sci 4, 15 (2006).

Scheele, J. S., Rhee, J. M. & Boss, G. R. Determination of absolute amounts of GDP and GTP bound to Ras in mammalian cells: comparison of parental and Ras-overproducing NIH 3T3 fibroblasts. Proc Natl Acad Sci U S A 92, 1097-1100 (1995).

Paradela, A. & Albar, J. P. Advances in the Analysis of Protein Phosphorylation. Journal of proteome research 7, 1809-1818 (2008).

Hunter, T. Protein kinases and phosphatases: the yin and yang of protein phosphorylation and signaling. Cell 80, 225-236 (1995).

Druker, B. J. et al. Five-year follow-up of patients receiving imatinib for chronic myeloid leukemia. N Engl J Med 355, 2408-2417 (2006).

Chahrour, O., Cairns, D. & Omran, Z. Small molecule kinase inhibitors as anti-cancer therapeutics. Mini Rev Med Chem 12, 399-411 (2012).

Zhang, J., Yang, P. L. & Gray, N. S. Targeting cancer with small molecule kinase inhibitors. Nat Rev Cancer 9, 28-39 (2009).

O'Hare, T., Zabriskie, M. S., Eiring, A. M. & Deininger, M. W. Pushing the limits of targeted therapy in chronic myeloid leukaemia. Nat Rev Cancer 12, 513-526 (2012).

Hamilton, A. et al. Chronic myeloid leukemia stem cells are not dependent on Bcr-Abl kinase activity for their survival. Blood 119, 1501-1510 (2012).

Niepel, M., Spencer, S. L. & Sorger, P. K. Non-genetic cell-to-cell variability and the consequences for pharmacology. Curr Opin Chem Biol 13, 556-561 (2009).

Corbin, A. S. et al. Human chronic myeloid leukemia stem cells are insensitive to imatinib despite inhibition of BCR-ABL activity. Journal of Clinical Investigation 121, 396-409 (2011).

Fallahi-Sichani, M., Honamejad, S., Heiser, L. M., Gray, J. W. & Sorger, P. K. Metrics other than potency reveal systematic variation in responses to cancer drugs. Nat Chem Biol 9, 708-714 (2013).

Clarke, M. F. et al. Cancer Stem Cells—Perspectives on Current Status and Future Directions: AACR Workshop on Cancer Stem Cells. Cancer Research 66, 9339-9344 (2006).

Huntly, B. J. & Gilliland, D. G. Leukaemia stem cells and the evolution of cancer-stem-cell research. Nat Rev Cancer 5, 311-321 (2005).

Reya, T., Morrison, S. J., Clarke, M. F. & Weissman, I. L. Stem cells, cancer, and cancer stem cells. Nature 414, 105-111 (2001).

Crews, L. A. & Jamieson, C. H. Chronic myeloid leukemia stem cell biology. Curr Hematol Malig Rep 7, 125-132 (2012).

Chu, S. et al. Persistence of leukemia stem cells in chronic myelogenous leukemia patients in prolonged remission with imatinib treatment. Blood 118, 5565-5572 (2011).

Hamilton, A. et al. BCR-ABL activity and its response to drugs can be determined in CD34+ CML stem cells by CrkL phosphorylation status using flow cytometry. Leukemia 20, 1035-1039 (2006).

Schulz, K. R., Danna, E. A., Krutzik, P. O. & Nolan, G. P. Single-cell phospho-protein analysis by flow cytometry. Curr Protoc Immunol Chapter 8, Unit 8.17.11-20 (2012).

Warsch, W. et al. High STAT5 levels mediate imatinib resistance and indicate disease progression in chronic myeloid leukemia. Blood 117, 3409-3420 (2011).

Hantschel, O. et al. BCR-ABL uncouples canonical JAK2-STAT5 signaling in chronic myeloid leukemia. Nat Chem Biol 8, 285-293 (2012).

Hughes, T. P. et al. Frequency of major molecular responses to imatinib or interferon alfa plus cytarabine in newly diagnosed chronic myeloid leukemia. N Engl J Med 349, 1423-1432 (2003).

Merante, S. et al. Outcome of four patients with chronic myeloid leukemia after imatinib mesylate discontinuation. Haematologica 90, 979-981 (2005).

Rousselot, P. et al. Imatinib mesylate discontinuation in patients with chronic myelogenous leukemia in complete molecular remission for more than 2 years. Blood 109, 58-60 (2007).

Phillips, R. M., Bair, E., Lawrence, D. S., Sims, C. E. & Allbritton, N. L. Measurement of protein tyrosine phosphatase activity in single cells by capillary electrophoresis. Anal Chem 85, 6136-6142 (2013).

Dovichi, N. J. & Hu, S. Chemical cytometry. Current Opinion in Chemical Biology 7, 603-608 (2003).

Bendall, S. C. et al. Single-Cell Mass Cytometry of Differential Immune and Drug Responses Across a Human Hematopoietic Continuum. Science 332, 687-696 (2011).

Edelstein, A., Amodaj, N., Hoover, K., Vale, R. & Stuurman, N. Computer control of microscopes using microManager. Curr Protoc Mol Biol Chapter 14, Unit14.20 (2010).

Carpenter, A. E. et al. CellProfiler: image analysis software for identifying and quantifying cell phenotypes. Genome Biol 7, R100 (2006).

Parthasarathy, R. Rapid, accurate particle tracking by calculation of radial symmetry centers. Nat Methods 9, 724-726 (2012).

Fichter, K. M., Flajolet, M., Greengard, P. & Vu, T. Q. Kinetics of G-protein-coupled receptor endosomal trafficking pathways revealed by single quantum dots. Proc Natl Acad Sci U S A 107, 18658-18663 (2010).

Scholl, B. et al. Single Particle Quantum Dot Imaging Achieves Ultrasensitive Detection Capabilities for Western Immunoblot Analysis. ACS Nano 3, 1318-1328 (2009).

Scott, D. W. On optimal and data-based histograms. Biometrika 66, 605-610 (1979).

Parzen, E. On Estimation of a Probability Density Function and Mode. Ann. Math. Statist. 33, 1065-1076 (1962).

Wahba, G. Optimal Convergence Properties of Variable Knot, Kernel, and Orthogonal Series Methods for Density Estimation. The Annals of Statistics 3, 15-29 (1975).

Silverman, B. W. Density Estimation for Statistics and Data Analysis. CRC Press (1986).

Jacob et al., Ultrasensitive proteomic quantitation of cellular signaling by digitized namnoparticle-protein counting, Nature Scientific Reports, 6.28163, 2016.

Mann, M., Hendrickson, R. C. & Pandey, A. Analysis of proteins and proteomes by mass spectrometry. Annu Rev Biochem 70, 437-473 (2001).

Pinaud, F., Clarke, S., Sittner, A. & Dahan, M. Probing cellular events, one quantum dot at a time. Nat Meth 7, 275-285 (2010).

Michalet, X. et al. Quantum dots for live cells, in vivo imaging, and diagnostics. Science 307, 538-544 (2005).

Kinoshita et al., Separation and detection of large phosphoproteins using Phos-tag SDS-PAGE, Nature Protocols, Sep. 24, 2009, vol. 4, No. 10.

Bodo et al., Quantitative In Situ Detection of Phosphoproteins in Fixed Tissues Using Quantum Dot Technology, J. Histochem. & Cytochem., 57(7), 701-708, 2009.

Casanova et al., Counting the Number of Proteins Coupled to Single Nanoparticles, J. Am. Chem. Soc., vol. 129, No. 42, pp. 12592-12593, 2007.

Lagerholm, et al., Analysis Method for Measuring Submicroscopic Distances with Blinking Quantum Dots, Biophysical Journal, vol. 91, pp. 3050-3060, Oct. 2009.

Tibbe et al., Optical Tracking and detection of immunomagnetically selected and aligned cells, Nature Biotechnology, vol. 17, Dec. 1999, pp. 1201-1213.

Dancey et al., Issues and Progress with Protein Kinase Inhibitors for Cancer Treatment, Nature Reviews Drug Discovery, Apr. 2003, vol. 2, pp. 296-313.

(56) References Cited

OTHER PUBLICATIONS

Chu et al., Persistence of leukemia stern cells in chronic myelogenous leukemia patients in prolonged remission with imatinib treatment, Blood, Nov. 17, 2011, vol. 118, No. 20, pp. 5565-5572.
Krutzik et al,, Phospho Flow Cytometry Methods for Analysis of Kinase Signaling in Cell Lines and Primary Human Blood Samples, Flow Cytometry Protocols, Methods in Molecular Biology, vol. 699, 2011, pp. 179-202.

\* cited by examiner

Drug treatment & antibody-QD labeling 3D multichannel image acquisition

Single-cell QD counting

Figure 7
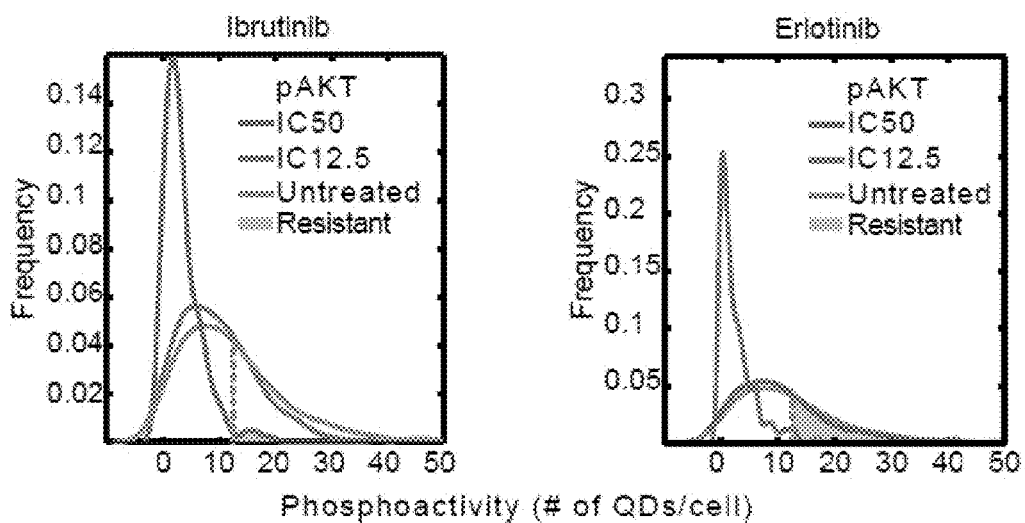
Figure 8A
| Cell type | CML 1 | CML 2 | CML 3 | CML 4 | CML 5 | Normal |
|---|---|---|---|---|---|---|
| Cell type | PB CD34+ | PB CD34+ | BM CD34+ | BM CD34+ | BM CD34+ | PB CD34- |
| Blast % | 1% | 4% | 1% | 3% | - | - |
| % BCR ABL+ cells (FISH) | 99% | 95% | 85% | 89% | - | - |
Figure 8B
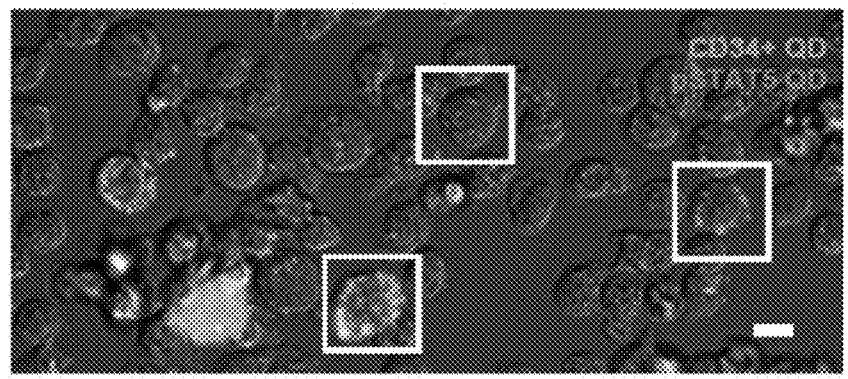

CELLULAR ACTIVITY QUANTIFICATION USING LABELED PROBES

CROSS REFERENCE TO RELATED APPLICATIONS

The present application claims priority to U.S. Provisional Application No. 62/081,926, filed Nov. 19, 2014.

ACKNOWLEDGMENT OF GOVERNMENT SUPPORT

This invention was made with United States government support under the terms of grant number GBMEN0125 awarded by the National Institutes of Health. The United States government has certain rights in this invention.

FIELD

The present disclosure relates to the field of detecting biomolecules. Specifically, this disclosure relates to systems and methods for quantifying cellular activity by detecting and counting biomolecules using discrete labels such as quantum dots, fluorescent dyes and other punctate labels.

BACKGROUND

Cellular signaling proteins are often present at low abundance within cells and therefore are difficult to quantitate reliably in single cells. For example, protein phosphorylation is one of the most ubiquitous and vital signaling processes; however, phosphoactivated proteins can exist at extremely low levels in single cells [1-3]. Moreover, many therapeutic compounds, such as kinase inhibitors, target and inhibit protein signaling [4-9], further decreasing the endogenous levels of signaling molecules, and posing additional challenges to detecting signaling molecules in single cells. Individual cells in a population are believed to contain differing levels of signaling molecules. Such cellular signaling heterogeneity may hold important keys to understanding the degree of effectiveness of some therapeutic treatments [10-14], as well as understanding important cell biological mechanisms, such as cellular proliferation and disease recurrence [15-19]. Thus, approaches that sensitively quantify the levels of key signaling molecules in single cells would contribute greatly to an improved characterization of disease states and a more complete assessment of therapeutic efficacy.

A technical challenge in measuring key single cell signaling states is overcoming limitations in attaining sufficient sensitivity necessary to reliably detect and quantify levels of activated signaling proteins above the background noise. Cell population-averaging techniques (e.g. immunoblotting, reverse protein arrays) boost detection sensitivity; however, such methods mask individual differences among cells. Fluorescence-activated cell sorting (FACS) is currently the method of choice for high-throughput single cell analysis and has yielded valuable insights into cellular signaling status of single cells [20-22]. However, approaches that provide increased sensitivity in the measurement of signaling activation in intact, single cells (as opposed to artifact, such as debris or aggregates), could provide important new, detailed information on subtle cellular signaling differences that has been previously overlooked [12].

SUMMARY

The present disclosure is directed to methods, apparatuses, and systems for quantifying cellular activity using discrete label complexes. In one example approach, a method for quantifying cellular activity in a sample containing intact cells having labeled complexes or other discrete labels comprises receiving images of the sample at a plurality of depths and detecting individual intact cells in the images of the sample at the plurality of depths. For each detected cell, the method may further comprise detecting and localizing discrete labels in the cell at each depth in the plurality of depths; calculating a total number of detected and localized labels in the cell; and calculating an activity level of the labeled complexes in the cell based on the total number of detected and localized labels in the cell. In some examples, a relative activity level of the labeled complexes may be calculated based on the number of detected and localized label complexes in each cell in the sample.

The present disclosure is also directed to a single-cell quantum dot phosphoassay (SC-QDP) platform that may be used to implement various methods described herein. For example, in some embodiments the SC-QDP platform disclosed herein may be used to implement various methods for quantifying cellular activity response to therapeutics, including combinations of therapeutics. In one example, a method for quantifying cellular activity response to a therapeutic may comprise treating cells in a sample with the therapeutic; providing the sample on a transparent base material; sequentially labeling protein targets in the sample with primary antibodies and secondary antibody quantum dot probes; and calculating activity levels of the protein targets in accordance with various embodiments disclosed herein.

Embodiments disclosed herein provide label complex imaging approaches that quantify cellular signaling by counting discrete labeled protein complexes in single cells. Embodiments disclosed herein may be used to measure low abundance proteins with sensitivity superseding conventional fluorescence averaging methods, and may be capable of assaying samples of limited cell number (e.g., less than 5,000), providing spatial information, and visually distinguishing intact single cells from artifacts. Embodiments disclosed herein may be implemented as multiplex assays and are broadly valuable for studying the cellular heterogeneity of signaling, drug resistance, and other important cellular processes in single cells to uncover differences in signaling among individual cells in disease and other biomedical contexts.

Disclosed are computer implemented methods of quantifying the activity of a target biomolecule in a sample. Examples of the activity of the target biomolecule include phosphorylation status, subcellular localization, and expression level. The sample can include one or more intact cells. The sample can be treated with a reagent that contains a label that can label a cellular structure such that the label can be localized within the cell. One example of such a label is a nanoparticle such as a quantum dot. The reagent also contains a binding component that binds the target biomolecule such as an antibody or nucleic acid. The target biomolecule has a first activity level that encompasses its activity level within an individual cell and a second activity level that encompasses its activity level within the entire sample. The method further involves receiving a set of images of the sample. The images are taken at a plurality of depths within the sample. A first cell is detected in the images at the plurality of depths and the label localized and detected at individual sites within the first cell at each depth in the plurality of depths. The method further involves calculating a total number of detected and localized labels within the first cell, calculating the first activity level of the target biomolecule within the cell based on the total number of detected and localized labels. The first activity level is calculated for each individual cell in a plurality of cells within the sample, said plurality up to and including all of the cells in the sample. The activity level of the target biomolecule in the sample is then calculated based on the number of detected and localized labels in the plurality of cells.

Also disclosed are methods of identifying a change in activity of a target biomolecule in response to a test compound. This method involves treating a first set of cells with a first concentration of the test compound, treating a second set of cells with a negative control, and contacting the sets of cells with a reagent that comprises a label that can label a cellular structure such that the label can be localized within the cell and a binding component that binds a target biomolecule. The activity of the target biomolecule in both sets of cells is then calculated using the method described above.

The above method can further involve a test compound comprising a potential therapeutic compound, a known therapeutic compound, or a combination of two or more known therapeutic compounds. The method can further involve treating a third set of cells with more than one concentration of the test compound and calculating the activity of the target biomolecule in the third set of cells. The method can further involve identifying a population of cells within the first set of cells that is resistant to the test compound. The method can further comprise contacting the cells with multiple reagents that bind to different target biomolecules and comprise labels of different colors such as quantum dots of different colors. The method can involve cells use of cells from a human cancer patient.

This Summary is provided to introduce a selection of concepts in a simplified form that are further described below in the Detailed Description. This Summary is not intended to identify key features or essential features of the disclosed subject matter, nor is it intended to be used to limit the scope of the disclosed subject matter. Furthermore, the disclosed subject matter is not limited to implementations that solve any or all disadvantages noted in any part of this disclosure.

BRIEF DESCRIPTION OF THE SEVERAL VIEWS OF THE DRAWINGS

Some of the drawings are better understood when presented in color which is not currently available in patent application publications. Applicants consider the color figures as part of the original disclosure and reserve the right to present color figures in later proceedings.

FIG. 7 is a set of two graphs showing example responses from two kinase inhibitors in the multi-panel SC-QDP screen shows heterogeneity of pAKT at baseline and following kinase inhibitor treatment in single AML MOLM-14 cells. Additional PDE plots showing pAKT activity following ibrutinib and erlotinib treatments. Broad width of the PDE and shaded purple area show, respectively, heterogeneity and resistance in pAKT levels at IC50 and IC12.5 in MOLM-14 cells. PDEs also illustrate how the sensitive quantitative capability of the SC-QDP reveals instances in which a kinase inhibitor (erlotinib) may exert inhibition of pAKT at an IC12.5 but has a reverse effect of pAKT activation at a higher IC50 concentration.

FIG. 8A is a table showing cell type, blast percentage and BCR-ABL1 positivity for CML specimens. PB=peripheral blood, BM=bone marrow, dashes=unavailable/not applicable data.

FIG. 8B is an image showing QD-labeled CML patient cells show heterogeneity in CD34 positivity (green) and pCRKL (magenta) expression. Framed areas show representative CD34+ (green) and CD34− cells, with varying numbers of pCRKL-QD probes in each cell (magenta). Scale bar=10 µm.

Figure 9A:
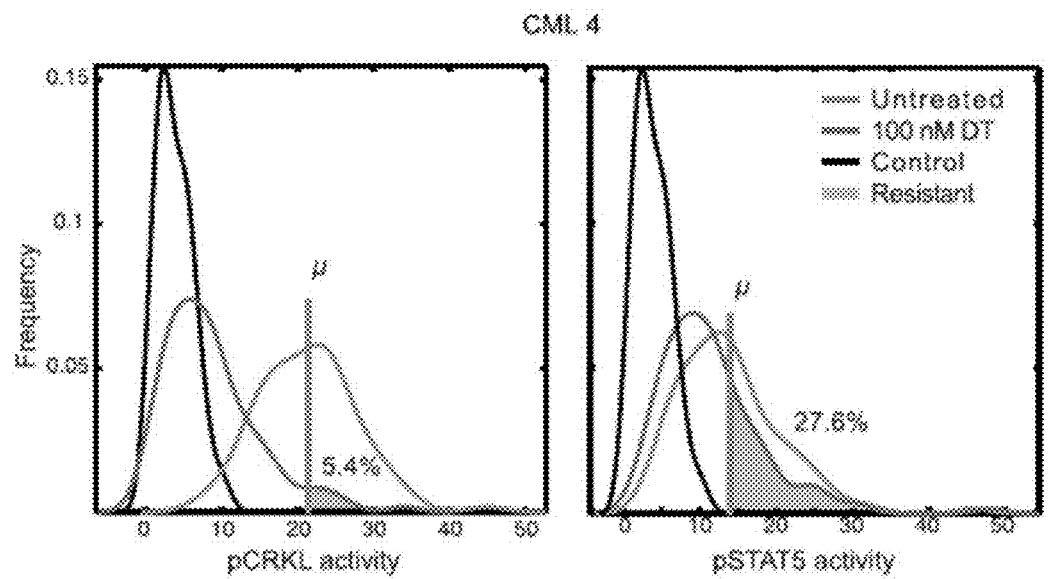
FIG. 9A is a set of two graphs of data demonstrating SC-QDP detection of dasatinib kinase inhibitor resistant CD34+ cells in two additional patients beyond those shown in FIG. 8C.
Figure 9B:
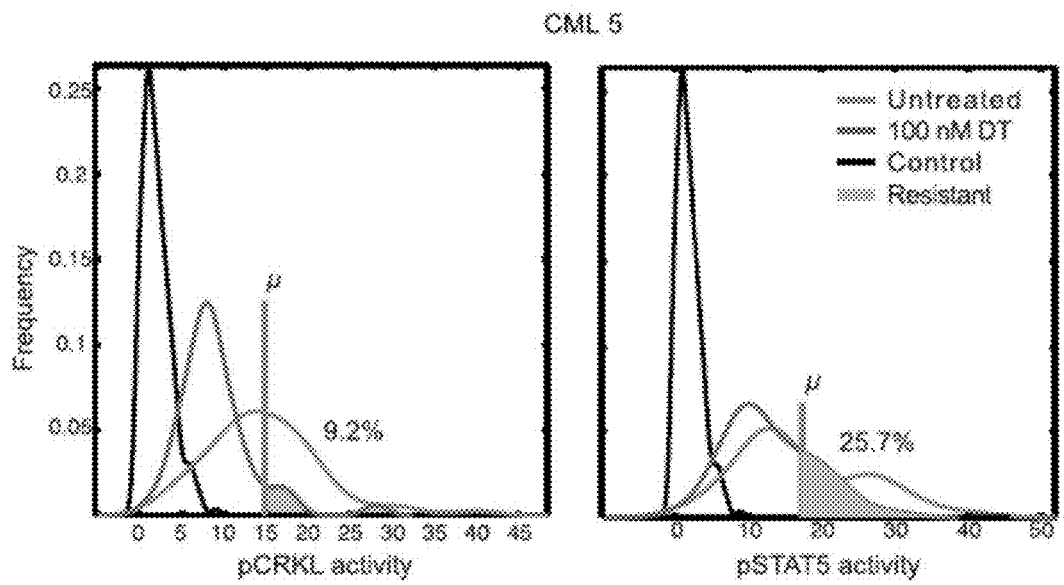
FIG. 9B is a set of two graphs of data demonstrating SC-QDP detection of dasatinib kinase inhibitor resistant CD34+ cells in two additional patients beyond those shown in FIG. 8C.

For both FIGS. 9A and 9B, Cells were treated with 100 nM dasatinib (DT) for 4 hours. Mean phosphoactivity levels ($\mu$ of untreated cells are marked by vertical green lines. Proportion of drug-treated cells with phosphoactivity levels above the mean value (right of $\mu$) is shaded, with percentage value identified. PDE curve (black) of the isotype control represents assay noise. The number of CD34+ cells sampled to quantify pCRKL activity for each of the two patients was n=91, 108 and 56, 45, for untreated and drug-treated conditions, respectively. The number of CD34+ cells sampled to quantify pSTAT5 activity for each of the two patients was n=100, 112 and 47, 47, for untreated and drug-treated conditions, respectively.

Figure 10:
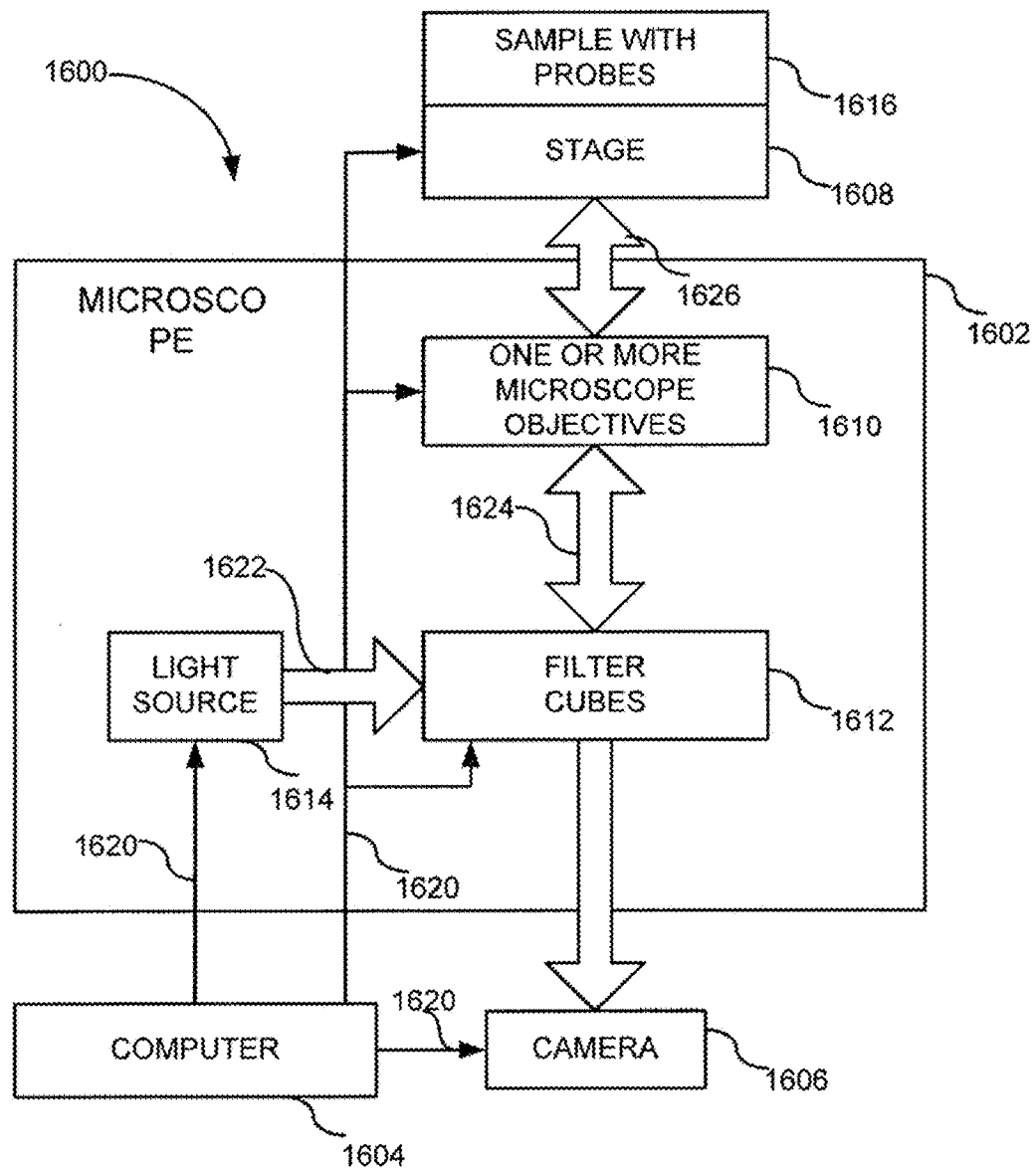

FIG. 10 is a block diagram of an example system used in automatically detecting and counting biomolecules.

Figure 11:
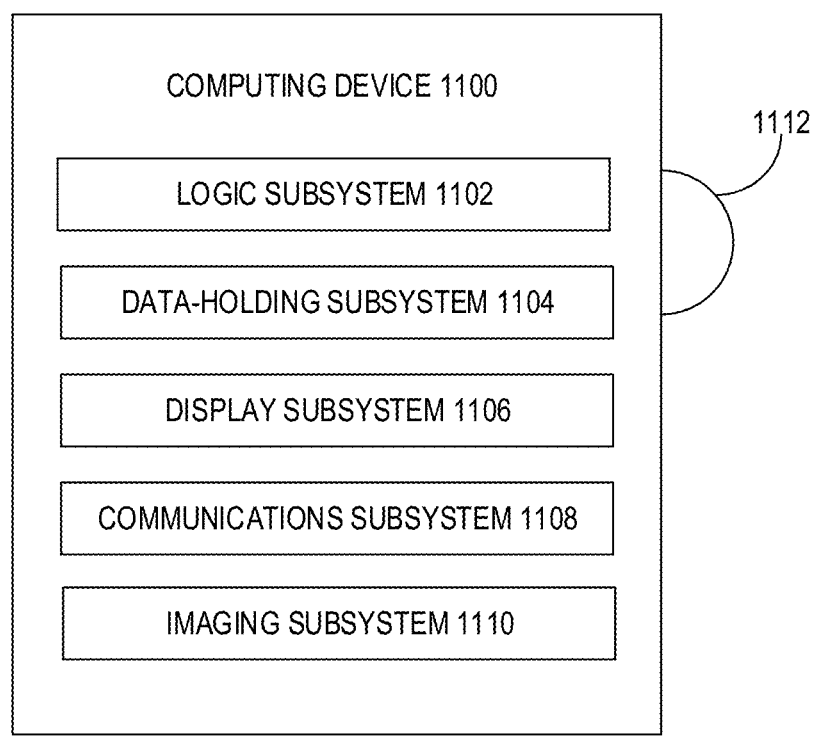

FIG. 11 schematically shows an example computing system in accordance with the disclosure.

Figure 12A:
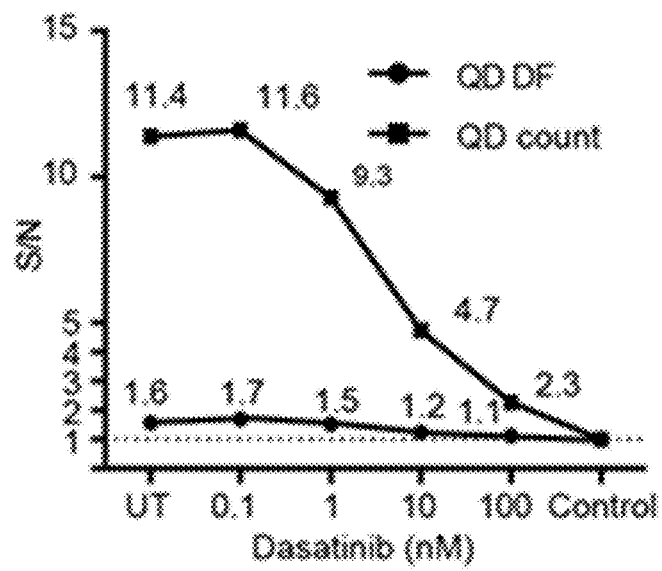

FIG. 12A is a plot of signal-to-noise (S/N) ratio for pCRKL quantification in K562 cells comparing the SC-QDP method of discrete nanoparticle counting (QD count) to the method of summing diffuse QD fluorescence (QD DF) in single cells, for a range of dasatinib drug concentrations. S/N is calculated by dividing the pCRKL level of each dasatinib-treated condition by the pCRKL levels of the isotype control. UT is untreated cells. Dashed line is isotype control value. Numbers of cells sampled: 142, 159, 130, 117, 130, and 181 (left to right, x-axis).

Figure 12B:
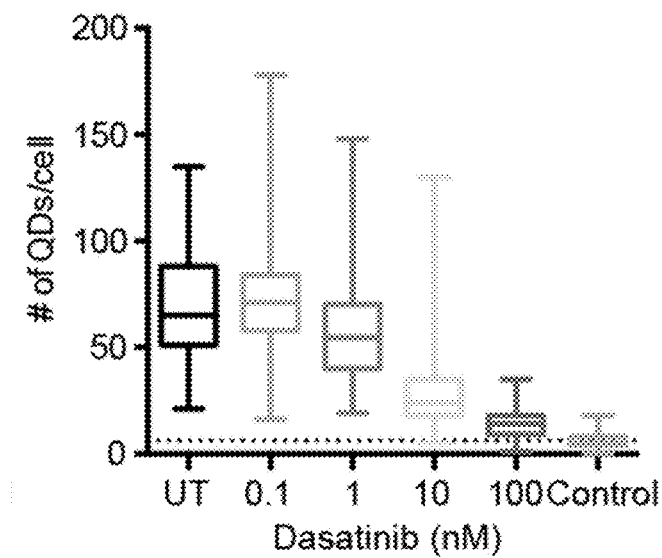

FIG. 12B is a box plot showing the absolute values of numbers of QDs/per cell for the SC-QDP discrete nanoparticle counting data from which signal to noise ratio values were computed in a). Dashed line represents the background noise and is the QD count for the isotype control.

Figure 12C:
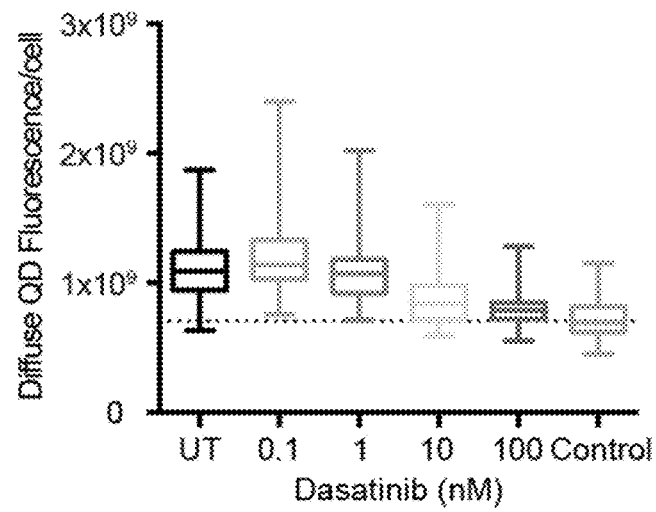

FIG. 12C is a box plot showing the absolute values for the total diffuse QD fluorescence per cell for a range of dasatinib concentrations. Dashed line represents the background noise and is the total diffuse fluorescence for the isotype control.

For both FIGS. 12B and 12C, boxes represent 25-75th percentile, middle line in the box is median value, and the upper and lower whiskers are maximum and minimum values. Numbers of K562 cells sampled are same as given in panel as FIG. 12A.

Figure 12D:
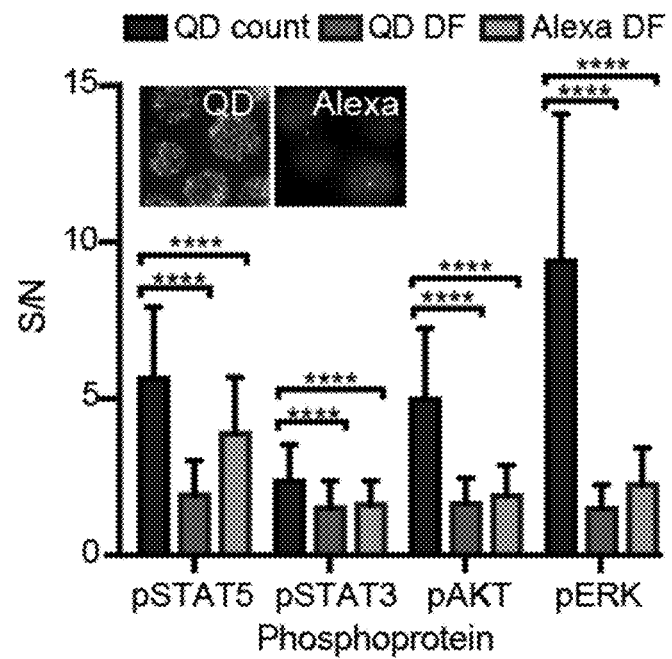

FIG. 12D is a graph of Single-cell phosphoquantification using the SC-QDP method of discrete nanoparticle probe counting produces superior detection sensitivity compared to quantitation of QD diffuse fluorescence per cell (DF) and Alexa 488 DF per cell. Phosphoactivity levels (y-axis) computed in single untreated K562 cells for pSTAT5, pSTAT3, pERK and pAKT. S/N ratio calculated by normalizing the phosphoactivity levels in untreated cells to the isotype control. Error bars are standard deviation. Mean values of S/N for bar plots (left to right) are: (QD count) 5.6,2.4,5.0,9.4; (QD diffuse fluorescence) 1.9,1.5,1.7,1.5 and (Alexa diffuse fluorescence) 3.9,1.6,1.9,2.3). p values are calculated by the Holm-Sidak multiple comparison test; each pair of comparisons denoted by the brackets (asterisks denote p value ≤0.0001). Inset shows representative images of pCRKL labeling by QD655 and Alexa 488 reporters in untreated K562 cells. The same primary phosphoantibody used for QD and Alexa 488 labeling. Numbers of cells sampled are n=637 (+/−169) for QD-labeling, and n=940 (+/−118) for the Alexa 488-labeling.

DETAILED DESCRIPTION

The following detailed description is directed to methods, apparatuses, and systems for quantifying cellular activity using nanoparticle probes, e.g., quantum dots. In the following detailed description, reference is made to the accompanying drawings which form a part hereof, and in which are shown by way of illustration embodiments that may be practiced. It is to be understood that other embodiments may be utilized and structural or logical changes may be made without departing from the scope of this disclosure. Therefore, the following detailed description is not to be taken in a limiting sense. Various operations may be described as multiple discrete operations in turn, in a manner that may be helpful in understanding embodiments; however, the order of description should not be construed to imply that these operations are order dependent.

Unless otherwise noted, technical terms used throughout this disclosure are used according to conventional usage. Definitions of common terms in molecular biology may be found in Benjamin Lewin, Genes VII, published by Oxford University Press, 2000 (ISBN 019879276X); Kendrew et al. (eds.), The Encyclopedia of Molecular Biology, published by Blackwell Publishers, 1994 (ISBN 0632021829); Robert A. Meyers (ed.), Molecular Biology and Biotechnology: a Comprehensive Desk Reference, published by Wiley, John & Sons, Inc., 1995 (ISBN 0471186341); and George P. Rédei, Encyclopedic Dictionary of Genetics, Genomics, and Proteomics, 2nd Edition, 2003 (ISBN: 0-471-26821-6). To facilitate review of the various embodiments of the invention, the following explanations of specific terms are provided:

Antibody: A polypeptide including at least a light chain or heavy chain immunoglobulin variable region which specifically recognizes and binds an epitope of an antigen or a fragment thereof. Antibodies are composed of a heavy and a light chain, each of which has a variable region, termed the variable heavy (VH) region and the variable light (VL) region. Together, the VH region and the VL region are responsible for binding the antigen recognized by the antibody. The VH and VL regions can be further segmented into complementarity determining regions (CDRs) and framework regions. The CDRs (also termed hypervariable regions) are the regions within the VH and VL responsible for antibody binding.

The term "antibody" encompasses intact immunoglobulins, as well the variants and portions thereof, such as Fab fragments, Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker. In dsFvs the chains have been mutated to introduce a disulfide bond to stabilize the association of the chains. The term also includes genetically engineered forms such as chimeric antibodies, heteroconjugate antibodies (such as, bispecific antibodies). See also, Pierce Catalog and Handbook, 1994-1995 (Pierce Chemical Co., Rockford, Ill.); Kuby, J., *Immunology,* 3rd Ed., W.H. Freeman & Co., New York, 1997. The term also includes monoclonal antibodies (all antibody molecules have the same VH and VL sequences and therefore the same binding specificity) and polyclonal antisera (the antibodies vary in VH and VL sequence but all bind a particular antigen such as a tissue antigen.)

Contacting: Placement in direct physical association, including contacting of a solid with a solid, a liquid with a liquid, a liquid with a solid, or either a liquid or a solid with a cell or tissue, whether in vitro or in vivo. Contacting can occur in vitro with isolated cells or tissue or in vivo by administering to a subject.

Control: A reference standard. A control can be a test compound that is known to affect a target biomolecule (positive control.) A control can also be a test compound known not to affect a target biomolecule, such as the vehicle in which the test compound is provided, otherwise lacking the test compound (negative control).

Label: A label may be any substance capable of aiding a machine, detector, sensor, device, column, or enhanced or unenhanced human eye from differentiating a labeled composition from an unlabeled composition. Labels may be used for any of a number of purposes and one skilled in the art will understand how to match the proper label with the proper purpose. Examples of uses of labels include purification of biomolecules, identification of biomolecules, detection of the presence of biomolecules, detection of protein folding, and localization of biomolecules within a cell, tissue, or organism. Examples of labels include but are not limited to: radioactive isotopes or chelates thereof; dyes (fluorescent or nonfluorescent), stains, enzymes, nonradioactive metals, magnets, protein tags, any antibody epitope, any specific example of any of these; any combination between any of these, or any label now known or yet to be disclosed. A label may be covalently attached to a biomolecule or bound through hydrogen bonding, Van Der Waals or other forces. A label may be covalently or otherwise bound to the N-terminus, the C-terminus or any amino acid of a polypeptide or the 5' end, the 3' end or any nucleic acid residue in the case of a polynucleotide.

In some examples, the label can be any label that can be localized within a cell. One example of such a label is a nanoparticle, including a semiconductor nanocrystal, also termed a quantum dot. In still further examples, labels include compounds smaller than a nanoparticle (such as a fluorescent polymer) that allow localization of the label within the cell. One of skill in the art would be able to use the methods described in this disclosure to test whether or not a sub nanoparticle label now known or yet to be disclosed can be used in the claimed methods.

Nanoparticles: Particles having maximum dimensions of about 1000 nanometers (nm) in any direction, meaning that the particle does not have any dimension that exceeds 1000 nm. In some examples, a nanoparticle has maximum dimensions of about 100 nm or less in any direction. An example of a nanoparticle is a quantum dot, but other examples include iron oxide or gold nanoparticles. Examples of methods of making gold nanoparticles are disclosed in U.S. Patent Publication 2005/0120174. Nanoparticles used as the nanoparticle probes of the present disclosure can be of any shape (such a spherical, tubular, pyramidal, conical or cubical). The spherical surface provides a substantially smooth and predictable high surface to volume ratio that can be optimized for controlled attachment of specific binding agents such as antibodies, with the bound agents extending substantially radially outwardly from the surface of the sphere.

Nucleic acid molecule (or sequence): A deoxyribonucleotide or ribonucleotide polymer including without limitation, cDNA, mRNA, genomic DNA, and synthetic (such as chemically synthesized) DNA or RNA. The nucleic acid molecule can be double stranded (ds) or single stranded (ss). Where single stranded, the nucleic acid molecule can be the sense strand or the antisense strand. Nucleic acid molecules can include natural nucleotides (such as A, T/U, C, and G), and can also include analogs of natural nucleotides. In one embodiment, a nucleic acid molecule is an aptamer.

Peptide/Protein/Polypeptide: All of these terms refer to a polymer of amino acids and/or amino acid analogs that are joined by peptide bonds or peptide bond mimetics. In one embodiment, a peptide is an aptamer.

Probe: Any molecule that specifically binds to a protein or nucleic acid sequence that is being targeted, and which can be identified (detected) so that the targets can then be detected. In particular examples, the probe is a nanoparticle probe that is labeled with a specific binding agent for binding the nanoparticle to a target biomolecule, such as a particular protein, peptide, small molecule, or nucleic acid molecule. In certain embodiments, the probe can be identified by the color, or composition of the nanoparticle, or by the wavelength of light, such as a color of light, emitted by the nanoparticle (as in a quantum dot). In certain embodiments, the probe includes a nanoparticle conjugated to an antibody or other specific-binding molecule that binds to a target protein. One example of a probe is an antibody.

Sample: A sample, such as a biological sample, is a sample obtained from a plant or animal subject. As used herein, biological samples include all clinical samples useful for detection via immunohistochemistry including cells, tissues, and bodily fluids, including tissues that are, for example, unfixed, frozen, fixed in formalin and/or embedded in paraffin. In particular embodiments, the biological sample is obtained from a subject, such as in the form of a tissue biopsy obtained from a subject with a tumor. Samples also include cell lines such as immortalized cell lines.

Semiconductor nanocrystals (quantum dots): Semiconductor crystalline nanospheres are also known as quantum dots, which are engineered, inorganic, semiconductor nanocrystals that fluoresce stably and possess a uniform generally spherical surface area that can be chemically modified to attach biomolecules to them, such as a specific binding agent. Generally, semiconductor nanocrystals can be prepared with relative monodispersity (for example, with the diameter of the core varying approximately less than 10% between semiconductor nanocrystals in the preparation), as has been described previously (Bawendi et al., J. Am. Chem. Soc. 115:8706, 1993). Semiconductor nanocrystals as known in the art have, for example, a core selected from the group consisting of CdSe, CdS, and CdTe (collectively referred to as "CdX"). These semiconductor nanocrystals have been used in place of organic fluorescent dyes as labels in immunoassays (as in U.S. Pat. No. 6,306,610) and as molecular beacons in nucleic acid assays (as in U.S. Pat. No. 6,500,622) among others.

Target biomolecule: A target biomolecule is a molecule of interest about which information is desired. A target biomolecule can be any molecule that is or once was part of a living organism. In several non-limiting examples, a target biomolecule is a polypeptide, a nucleic acid, a ligand, or a small molecule. In one example, the information desired is location of the biomolecule on or within a cell, such as a cell in a biological sample. In another example, the information desired is the presence or absence of the biomolecule, for example in a sample, such as a biological sample. In another example, the information desired is the presence, absence, and/or location of the target biomolecule in a gel, such as a composite gel. In another example, the information desired is the presence, absence, and/or location of the target biomolecule in on a membrane, such as a polyvinylidene fluoride (PVDF) membrane.

Test Compound: A test compound can be any compound that is suspected of affecting the activity of a target biomolecule. Examples of test compounds include small molecules, proteins, peptides, including any known or potential therapeutic compounds. A test compound can also be a compound known to affect target biomolecule activity that is used as a positive control. A test compound can also be a compound known not to affect target biomolecule activity that is used as a negative control. A test compound can comprise a mixture of more than one known or potential therapeutic compounds to be tested in combination including combinations of two or more, three or more, four or more or five or more known or potential therapeutic compounds.

Embodiments disclosed herein provide systems and methods for quantifying cellular activity in a sample. Embodiments disclosed herein provide systems and methods for counting nanoparticles in a sample. Embodiments disclosed herein provide systems and methods for quantifying cellular activity response to therapeutics. Quantifying a cellular activity response to therapeutics includes quantifying a cellular activity response to a combination of at least two or more therapeutic compounds, including at least three, at least four, or more than four therapeutic compositions. Combinations of therapeutic compositions can be administered to a cell, at the same time or sequentially.

In some embodiments, a plurality of different protein targets are labeled with a plurality of probes in one or more individual cells in a sample. In some non-limiting examples, individual cells in a sample are labeled with more than one probe, wherein at least one probe is directed to a first target biomolecule (for example a cell surface molecule or an intracellular molecule, such as a cytoplasmic or nuclear molecule) and at least one probe is directed to a second target biomolecule (for example, a cell surface molecule or an intracellular molecule). In other non-limiting examples, individual cells in a sample are labeled with at least three, at least four, at least five, at least six, at least seven, at least eight or more different probes directed to cell surface molecules, intracellular molecules, or combinations thereof.

In some embodiments, the labeled sample comprises cells of a single cell type that are homogeneously labeled or heterogeneously labeled. In other embodiments, the labeled sample comprises cells of more than one cell type, for example different types of normal cells, different types of disease cells, or combinations of normal and disease cells. In specific non-limiting examples, the sample comprises tumor cells and immune cells. Immune cells can be, for example, B cells, T cells, monocytes, macrophages, natural killer cells, and the like. Tumor cells can be from solid tumors (i.e breast, pancreatic, prostate tumors and the like) or liquid tumors (i.e. leukemia or lymphoma). The different cell types can be from a single individual or from different individuals.

In one example embodiment a computer-implemented method for quantifying cellular activity in a sample containing intact cells having nanoparticle-labeled complexes is provided. In some embodiments, the nanoparticles may comprise semiconductor nanocrystals (quantum dots). In some embodiments, the nanoparticle-labeled complexes may comprise protein complexes labeled with antibody-quantum dot probes. In other embodiments, the nanoparticle-labeled complexes may comprise nanoparticle-labeled nucleic acid molecules, e.g., deoxyribonucleic acid (DNA) or ribonucleic acid (RNA). The method may comprise receiving images, e.g., fluorescent micrographs, of the sample at a plurality of depths. In some examples, the images of the sample at the plurality of depths may comprise z-stacks at multiple fields of view of the sample. Individual intact cells may be detected in the images of the sample at the plurality of depths. For example, detecting individual intact cells in the images of the sample at the plurality of depths may comprise detecting a nucleus and plasma membrane of each individual intact cell via a threshold-based intensity algorithm and a membrane expansion cell segmentation algorithm. For each detected cell, discrete nanoparticles may be detected and localized in the cell at each depth in the plurality of depths. For example, when the nanoparticles comprise quantum dots and the images comprise fluorescent micrographs, detecting and localizing discrete nanoparticles in a cell at each depth in the plurality of depths may comprise applying a spatial band-pass filter, detecting localized maxima (e.g., using centroid localization or radial symmetry localization), and calculating a position of each quantum dot in the cell at each depth in the plurality of depths. For each detected cell, a total number of detected and localized nanoparticles in the cell may be calculated. For example, calculating the total number of detected and localized nanoparticles in each cell may comprise summing pixel values corresponding to the cell from all depths in the plurality of depths and subtracting a global background value for each field of view. For example, the global background value for each field of view may be calculated as a mean of a minimum pixel value corresponding to each y-column of the field of view. For each detected cell, an activity level of the nanoparticle-labeled complexes in the cell may be calculated based on the total number of detected and localized nanoparticles in the cell. For example, when the nanoparticle-labeled complexes comprise phosphoactivated proteins, the activity level of the quantum dot labeled complexes may comprise phosphoactivity levels. The method may further comprise calculating a relative activity level of the nanoparticle-labeled complexes based on the number of detected and localized nanoparticles in each cell in the sample.

Embodiments disclosed herein are directed to performing quantum dot counting and cellular activity estimation on a per-cell basis. As described herein, cellular activity may be different for different cells. Thus, in some examples, a method according to various embodiments may further comprise for a first detected cell: detecting and localizing discrete nanoparticles in the first cell at each depth in the plurality of depths; calculating a first total number of detected and localized nanoparticles in the first cell; and calculating a first activity level of the nanoparticles labeled complexes in the first cell based on the total number of detected and localized nanoparticles in the first cell. In this example, the method may further comprise for a second detected cell different from the first cell: detecting and localizing discrete nanoparticles in the second cell at each depth in the plurality of depths; calculating a second total number of detected and localized nanoparticles in the second cell; and calculating a second activity level of the nanoparticles labeled complexes in the second cell based on the total number of detected and localized nanoparticles in the second cell, where the second total number of detected and localized nanoparticles is different from the first total number of detected and localized nanoparticles and the second activity level is different from the first activity level.

Embodiments of the methods disclosed herein may further comprise calculating a continuous probability density function of activity levels of single cells sampled from the total cell population in the sample based on the number of detected and localized nanoparticles in each cell. For example, the continuous probability density function may be calculated using a Gaussian kernel density estimation. In some examples, the continuous probability density function may comprise frequencies of single cells as a function of activity levels of the nanoparticle-labeled complexes. The relative activity level of the nanoparticle-labeled complexes may be calculated based on the continuous probability density function of activity levels of single cells sampled from the total cell population in the sample.

Embodiments disclosed herein are also directed to quantifying cellular activity response to therapeutics, e.g., using a single-cell quantum dot phosphoassay (SC-QDP) platform. For example, a method for quantifying cellular activity response to a therapeutic may comprise: treating cells in a sample with the therapeutic; providing the sample on a transparent base material (e.g., a cover glass chamber); sequentially labeling protein targets in the sample with primary antibodies and secondary antibody quantum dot probes; and calculating activity levels of the protein targets in accordance with various embodiments disclosed herein. In some examples, the protein targets may comprise phosphoactivated proteins and the therapeutic may comprise a kinase inhibitor. A method according to various embodiments may further comprise sequentially labeling a plurality of different protein targets in the sample with different primary antibodies and different secondary antibody quantum dot probes, where the different quantum dot probes have different colors; and for each protein target in the plurality of different protein targets, calculating activity levels of the protein target in accordance various embodiments disclosed herein.

Embodiments described herein may be used to detect and quantify activities of target biomolecules (such as polypeptides, nucleic acid molecules, and other biomolecules). The systems and methods described herein allow for counting quantum dot-tagged proteins on transparent base materials, e.g., one or more cover glass chambers, optically transparent membranes, slides, etc. The presence of or activity of any protein in low abundance in a cell or sample that requires high sensitivity can be detected and quantified.

In one embodiment, target biomolecules are labeled with a nanoparticle probe that includes a detectable nanoparticle, such as a fluorescent semiconductor nanocrystal (quantum dot). Target biomolecules can be labeled in situ in cells, or cell lysates or other biological solutions. The labeled biomolecules may be placed on a transparent base material, such as a membrane, slide, or chamber. In some embodiments, the transparent base material may be loaded onto a stage (e.g., an X-Y stage or X-Y-Z stage), which can automatically reposition the transparent base for image capture at varying locations. A microscope can be used for providing a light source to cause the nanocrystals to fluoresce and for providing the magnification needed for image capture. Once one or more images are captured, the nanoparticles can be automatically counted using post-processing software that maintains a total count across multiple images, if desired.

In embodiments, the transparent base material can be a transparent chamber, membrane, or slide in a variety of formats. For example, a protein microarray can be used wherein the nanocrystals are transferred to a slide, such as a glass slide. As another example, a multi-well cover glass chamber may be used.

Embodiments disclosed herein provide nanoparticle imaging approaches that quantify cellular signaling by counting discrete quantum dot-tagged protein complexes in single cells. Embodiments disclosed herein may be used to measure low abundance proteins with sensitivity superseding conventional fluorescence averaging methods, and may be capable of assaying samples of limited cell number, and visually distinguishing intact single cells from artifacts. Embodiments disclosed herein can be useful for detecting protein or protein fragments in small populations of cells. Such detection of small numbers of cells can be useful in certain applications, such as in a solid tumor biopsy, where small numbers of cells is important. Embodiments disclosed herein are broadly valuable for studying the cellular heterogeneity of signaling, drug resistance, and other important cellular processes in single cells and may be used to uncover differences in signaling among individual cells in disease and other biomedical contexts.

In some embodiments, a nanoparticle probe used to label a target complex includes a specific binding agent that specifically binds the target complex of interest. In some embodiments, the specific binding agent is an antibody, a ligand, an aptamer, or a peptide. The specific binding agent can be conjugated directly to the nanoparticle. Alternatively, the specific binding agent can be operably linked to the nanoparticle with a linker. Methods for the conjugation of nanoparticles and specific binding agents, for example via a linker, are given below. In some embodiments, the linker is streptavidin, avidin, biotin, or a combination thereof.

The present methods are applicable for any sample for which information about a biomolecule of interest is desired, for example to detect the presence of and/or location of the biomolecule of interest, the interaction partner(s) of the biomolecule of interest, cellular activity levels of the biomolecule of interest, etc. In the case of cellular samples, such as tissue samples (for example cultured cells), the sample can be contacted with a nanoparticle probe and then lysed or homogenized to solubilize or suspend the constituent biomolecules, such as the target biomolecule. Optionally, the sample can be further processed, for example to remove particulate matter or debris, or partially purified to isolate a class of molecules (such as proteins) of interest. In the case of biological fluid samples, the fluid can be partially purified or concentrated if desired.

In some embodiments, complexes in a sample may be labeled with a detectable nanoparticle comprising a semiconductor nanocrystal (for example, a semiconductor nanocrystal with maximum dimensions between about 5 nm and 1000 nm) that emits a detectable electromagnetic signal, such as a characteristic emission spectrum, for example light. The detectable electromagnetic signal emitted by the semiconductor nanocrystal can be used to identify the target biomolecule of interest, for example to identify the position (location) of the target biomolecule of interest on or within a cell. In one embodiment, the characteristic emission spectrum of a semiconductor nanocrystal identifies the presence or position (location) of the target biomolecule on or within a cell.

In embodiments, biological samples, including tissue samples or cultured cells (or homogenates or lysates) or other biofluids containing a single or multiple target proteins may be contacted with nanoparticle probes, for example semiconductor nanocrystals conjugated to specific binding agents (such as antibodies, ligands, peptides, or aptamers).

Nanoparticles are discrete structures having dimensions less than or equal to about 1000 nm (for example, less than about 500 nm, less than about 400 nm, less than about 300 nm, less than about 200 nm, less than about 100 nm, less than about 50 nm, less than about 20 nm, less than about 10 nm, or even less than about 1 nm, for example 0.1 nm-1000 nm, such as 0.1-100 nm, 0.1-50 nm or 0.1-10 nm). Typically a nanoparticle has three dimensions on the nanoscale. That is, the particle is between 0.1 and 1000 nm in each spatial dimension, such as any integer or integer fraction between 0.1 and 1000 nm. In particular examples, the particle is between 0.1 and 100 nm in each spatial dimension, such as any integer or integer fraction between 0.1 and 100 nm.

An example of a nanoparticle is a semiconductor nanocrystal, but other examples include various polymers, silica (including dye-doped silica), and metal oxides and metals, such as iron oxide and gold nanoparticles. Examples of methods of making gold nanoparticles are disclosed in U.S. Patent Publication 2005/0120174. Nanoparticles used as the nanoparticle probes of the present disclosure can be of any shape (such a spherical, tubular, pyramidal, conical or cubical), but particularly suitable nanoparticles are spherical. The spherical surface provides a substantially smooth and predictably oriented surface for the attachment of specific binding agents such as antibodies, with the attached agents extending substantially radially outwardly from the surface of the sphere.

In some embodiments, the nanoparticle may be spaced from a specific binding agent (such as an agent that binds a target biomolecule, for example an antibody) by a linker. The specific binding agents may be linked to the nanoparticle by linkers that space the binding agent slightly from the nanoparticle. As a result, multiple specific binding agents can be distributed over the surface of the nanoparticle to form a three dimensional binding surface that efficiently interacts with targets biomolecules, such as proteins.

In certain embodiments, the detectable nanoparticles are semiconductor nanocrystals, also known as quantum dots (QUANTUM DOTS™). Semiconductor nanocrystals are nanoparticles having size-dependent optical and/or electrical properties. When semiconductor nanocrystals are illuminated with a primary energy source, a secondary emission of energy occurs of a frequency that corresponds to the bandgap of the semiconductor material used in the semiconductor nanocrystal. In quantum confined particles, the bandgap energy is a function of the size and/or composition of the nanocrystal. As the band gap energy of such semiconductor nanocrystals varies with size, coating and/or material of the crystal, populations of these crystals can be produced that have a variety of spectral emission properties. Furthermore, the intensity of the emission of a particular wavelength can be varied, thereby enabling the use of a variety of encoding schemes (e.g., different colors). A spectral label defined by a combination of semiconductor nanocrystals with differing emission signals can be identified from the characteristics of the spectrum emitted by the label when the semiconductor nanocrystals are energized. Semiconductor nanocrystals with different spectral characteristics are described in for example, U.S. Pat. No. 6,602,671, which is incorporated herein by reference.

A mixed population of semiconductor nanocrystals of various sizes and/or compositions can be excited simultaneously using a single wavelength of light and the detectable luminescence can be engineered to occur at a plurality of wavelengths. The luminescent emission is related to the size and/or the composition of the constituent semiconductor nanocrystals of the population. Furthermore, semiconductor nanocrystals can be made highly luminescent through the use of a shell material which efficiently encapsulates the surface of the semiconductor nanocrystal core. A "core/shell" semiconductor nanocrystal has a high quantum efficiency and significantly improved photochemical stability. The surface of the core/shell semiconductor nanocrystal can be modified to produce semiconductor nanocrystals that can be coupled to a variety of biological molecules or substrates by techniques described in, for example, Bruchez et al. Science 281:2013-2016, 1998, Chan et al. Science 281: 2016-2018, 1998, and U.S. Pat. No. 6,274,323, which are incorporated herein by reference.

Semiconductor nanocrystals can be used to detect or track a single target, such as a target biomolecule (for example, a protein expressed by a cell). Additionally, a mixed population of semiconductor nanocrystals can be used for either simultaneous detection of multiple targets (such as, different target biomolecules) or to detect particular biomolecules and/or other items of interest. For example, compositions of semiconductor nanocrystals comprising one or more particle size distributions having characteristic spectral emissions can be used to identify particular target biomolecules of interest. The semiconductor nanocrystals can be tuned to a desired wavelength to produce a characteristic spectral emission by changing the composition and size, or size distribution, of the semiconductor nanocrystal. The information encoded by the semiconductor nanocrystals can be spectroscopically decoded, thus providing the location and/or identity of the particular item or component of interest.

Semiconductor nanocrystals for use in the subject methods are made using techniques known in the art. Examples of semiconductor nanocrystals suitable for use in the methods disclosed herein are available commercially, for example, from Invitrogen (Carlsbad, Calif.), Quantum Dot Corporation (Hayward, Calif.), and Evident Technologies (Troy, N.Y.). Semiconductor nanocrystals useful in the disclosed methods include nanocrystals of Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe as well as mixed compositions thereof; as well as nanocrystals of Group III-V semiconductors such as GaAs, InGaAs, InP, and InAs and mixed compositions thereof. The use of Group IV semiconductors such as germanium or silicon, or the use of organic semiconductors, can also be feasible under certain conditions. The semiconductor nanocrystals can also include alloys comprising two or more semiconductors selected from the group consisting of the above Group III-V compounds, Group II-VI compounds, Group IV elements, and combinations of the same. Formation of semiconductor nanocrystals of various compositions are disclosed for example in U.S. Pat. Nos. 6,927,069, 6,855,202, 6,689,338, 6,306,736, 6,225,198, 6,207,392; 6,048,616; 5,990,479; 5,690,807; 5,571,018; 5,505,928; 5,262,357 (all of which are incorporated herein in their entireties); as well as PCT Publication No. 99/26299 (published May 27, 1999).

The semiconductor nanocrystals described herein have a capability of absorbing radiation over a broad wavelength band. This wavelength band includes the range from gamma radiation to microwave radiation. In addition, these semiconductor nanocrystals have a capability of emitting radiation within a narrow wavelength band of about 40 nm or less, preferably about 20 nm or less, thus permitting the simultaneous use of a plurality of differently colored semiconductor nanocrystal probes without overlap (or with a small amount of overlap) in wavelengths of emitted light when exposed to the same energy source. Both the absorption and emission properties of semiconductor nanocrystals can serve as advantages over dye molecules which have narrow wavelength bands of absorption (such as about 30-50 nm) and broad wavelength bands of emission (such as about 100 nm) and broad tails of emission (such as another 100 nm) on the red side of the spectrum. Both of these properties of dyes impair the ability to use a plurality of differently colored dyes when exposed to the same energy source.

The frequency or wavelength of the narrow wavelength band of light emitted from the semiconductor nanocrystal can be further selected according to the physical properties of the semiconductor nanocrystal. There are many alternatives to selectively manipulate the emission wavelength of semiconductor nanocrystals. These alternatives include: (1) varying the composition of the nanocrystal, and (2) adding a plurality of shells around the core of the nanocrystal in the form of concentric shells. Thus, as one of ordinary skill in the art will realize, a particular composition of a semiconductor nanocrystal as listed above will be selected based upon the spectral region being monitored. For example, semiconductor nanocrystals that emit energy in the visible range include, but are not limited to, CdS, CdSe, CdTe, ZnSe, ZnTe, GaP, and GaAs. Semiconductor nanocrystals that emit energy in the near IR range include, but are not limited to, InP, InAs, InSb, PbS, and PbSe. Finally, semiconductor nanocrystals that emit energy in the blue to near-ultraviolet include, but are not limited to, ZnS and GaN. A nanocrystal composed of a 3 nm core of CdSe and a 2 nm thick shell of CdS will emit a narrow wavelength band of light with a peak intensity wavelength of 600 nm. In contrast, a nanocrystal composed of a 3 nm core of CdSe and a 2 nm thick shell of ZnS will emit a narrow wavelength band of light with a peak intensity wavelength of 560 nm. It should be noted that different wavelengths can also be obtained in multiple shell type semiconductor nanocrystals by respectively using different semiconductor nanocrystals in different shells, for example, by not using the same semiconductor nanocrystal in each of the plurality of concentric shells.

Additionally, the emission spectra of semiconductor nanocrystals of the same composition can be tuned by varying the size of the particle with larger particles tending to emit at longer wavelengths. For example, semiconductor nanocrystals that emit at different wavelengths based on size (565 nm, 655 nm, 705 nm, or 800 nm emission wavelengths), which are suitable for use the methods disclosed herein are available from Invitrogen (Carlsbad, Calif.).

Optionally, the emission of semiconductor nanocrystals can be enhanced by overcoating the particle with a material that has a higher bandgap energy than the semiconductor nanocrystal core. Suitable materials for overcoating are disclosed in U.S. Pat. No. 6,274,323, which is incorporated herein by reference. These and many other aspects of semiconductor nanocrystal design are disclosed in U.S. Pat. Nos. 5,990,479; 6,114,038; 6,207,392; 6,306,610; 6,500,622; 6,709,929; 6,914,256; and in U.S. Patent Publication 2003/0165951, which are incorporated herein by reference to the extent they disclose design of semiconductor nanocrystals.

The methods disclosed herein involve nanoparticles, such as semiconductor nanocrystals, associated with a specific binding molecule or affinity molecule that binds to a biomolecule of interest, such as a biomolecule expressed by a cell, for example a protein. Without limitation, nanoparticle conjugates can include any specific binding molecules (or molecular complexes), linked to a nanoparticle, which can interact with a biological target, to detect biological processes, or reactions, as well as alter biological molecules or processes. Typically, the specific binding molecules physically interact with a biomolecule. Preferably, the interactions are specific. The interactions can be, but are not limited to, covalent, noncovalent, hydrophobic, hydrophilic, electrostatic, van der Waals, or magnetic interactions. In certain examples, the specific binding molecules are antibodies. However, one of skill in the art will recognize that the class of specific binding agents includes a wide variety of agents that are capable of interacting (binding) specifically to a biomolecule, such as a biomolecule expressed by a cell, such as receptors and receptor analogues, ligands, including small molecule ligands and other binding partners.

Nanoparticles, such as semiconductor nanocrystals, of varying sizes (such as, from about 1 nm to 1000 nm), composition, and/or size distribution are conjugated to specific binding molecules which bind specifically to a target biomolecule of interest. The specific binding molecule is selected based on its affinity for the particular target biomolecule of interest. The affinity molecule can comprise any molecule capable of being linked to one or more nanoparticles that is also capable of specific recognition of a particular substance (such as a target biomolecule) of interest.

Semiconductor nanocrystals-bound to the biomolecular constituent of interest can be qualitatively or quantitatively detected under illumination, such as UV-illumination, using available detection technologies, such as fluorescence scanners and/or digital cameras. If desired different specific binding agents conjugated to semiconductor nanocrystals with different spectral properties can be used to detect different cellular components.

Separate populations of semiconductor nanocrystals can be produced that are identifiable based on their different spectral characteristics. In the context of the methods disclosed herein, separate populations of semiconductor nanocrystals with different emission spectra can be used to identify different biomolecules (for example, different proteins). The characteristic emissions can be observed as colors (if in the visible region of the spectrum) or can be decoded to provide information about the particular wavelength at which the discrete transition is observed. Likewise, for semiconductor nanocrystals producing emissions in the infrared or ultraviolet regions, the characteristic wavelengths that the discrete optical transitions occur at provide information about the identity of the particular semiconductor nanocrystal, and hence about the identity of biomolecule of interest. The color of light produced by a particular size, size distribution and/or composition of a semiconductor nanocrystal can be readily calculated or measured by methods which will be apparent to those skilled in the art. As an example of these measurement techniques, the bandgaps for nanocrystals of CdSe of sizes ranging from 12 Å to 115 Å are given in Murray et al., J. Am. Chem. Soc. 115:8706, 1993. These techniques allow ready calculation of an appropriate size, size distribution and/or composition of semiconductor nanocrystals and choice of excitation light source to produce a nanocrystal capable of emitting light device of any desired wavelength.

Methods and devices for eliciting and detecting emissions from semiconductor nanocrystals are well known in the art. In brief, a light source typically in the blue or UV range that emits light at a wavelength shorter than the wavelength to be detected is used to elicit an emission by the semiconductor nanocrystals. Numerous such light sources (and devices incorporating such light sources) are known in the art, including without limitation: deuterium lamps and xenon lamps equipped with filters, continuous or tunable gas lasers, such as argon ion, HeCd lasers, solid state diode lasers (for example, GaN, GaAs lasers), YAG and YLF lasers and pulsed lasers. The emissions of semiconductor nanocrystals can similarly be detected using known devices and methods, including without limitation, spectral imaging systems such as those disclosed in U.S. Pat. No. 6,759,235, which is incorporated herein by reference. Optionally, the emissions are passed through one or more filters or prisms prior to detection.

Aspects of this disclosure relate to kits for the counting target complexes and quantifying cellular activity in samples. One or more of the nanoparticle probes, therapeutic agents, and transparent base material(s) can be supplied in the form of a kit for use in the detection of target biomolecules of interest and the quantification of cellular activity as described herein. In such a kit, an appropriate amount of one or more nanoparticle probes may be provided in one or more containers. A nanoparticle probe may be provided suspended in an aqueous solution or as a freeze-dried or lyophilized powder, for instance. The nanoparticle probes that are supplied can be any conventional container that is capable of holding the supplied form, for instance, microfuge tubes, ampoules, or bottles. In other particular embodiments, the kit includes equipment, reagents, and/or instructions for labeling electrophoresing and detecting the target biomolecules of interest. Additionally, in some examples, the kit may include software configured to cause a computing device to perform acts of the various methods described herein.

The amount of the nanoparticle probes supplied in the kit can be any appropriate amount, and may depend on the target market to which the product is directed. For instance, if the kit is adapted for research or clinical use, the amount of each nanoparticle probe would likely be an amount sufficient for several labeling experiments. In certain embodiments, the nanoparticle probe includes a semiconductor crystal, such as a quantum dot. In some embodiments, the nanoparticle probe includes a specific binding agent (such as an antibody, a ligand, an aptamer, or a peptide) that specifically binds the target biomolecule of interest, such as a polypeptide. In some embodiments, the detectable nanoparticle is conjugated directly to the specific binding agent. In other embodiments, a linker is used to link the detectable nanoparticle and the specific binding agent. In specific embodiments, the linker is streptavidin, avidin, biotin or a combination thereof. In some examples, the nanoparticle probe conjugated to streptavidin, avidin, or biotin, such that the nanoparticle probe can be attached to a specific binding agent that is conjugated to streptavidin, avidin, or biotin.

EXAMPLES

The following examples are provided to illustrate particular features of certain embodiments. However, the particular features described below should not be construed as limitations on the scope of the invention, but rather as examples from which equivalents will be recognized by those of ordinary skill in the art.

The following examples demonstrate a nanoparticle imaging approach that quantifies cellular signaling by counting discrete quantum dot-tagged protein complexes in single cells. An example, single-cell quantum dot phosphoassay (SC-QDP) is described that measures low abundance proteins with sensitivity superseding conventional fluorescence averaging methods, is capable of assaying samples of limited cell number, and visually distinguishes intact single cells from artifacts. In these examples, the SC-QDP approach is used to capture phosphosignaling and show that: 1) many kinase inhibitors exert potent inhibition in the overall leukemic cell population, but drug-resistant cells expressing high levels of pERK and pAKT signaling are prevalent; and 2) chronic myeloid leukemia patients harbor drug-resistant CD34+ stem cells which exist at low frequency but possess high levels of pCRKL and pSTAT signaling. Since many important proteins are expressed at low levels, ultrasensitivity of the SC-QDP is broadly valuable for studying the cellular heterogeneity of signaling, drug resistance, and other important cellular processes in single cells.

Methods

Cell culture and kinase inhibitor treatment. Primary mononuclear cells (MNCs) were isolated from peripheral blood or bone marrow of newly diagnosed, untreated patients with chronic phase CML. MNCs were isolated by centrifugation through a Ficoll gradient, and red blood cells were lysed with 1×ACK (0.15 M NH4Cl, 10 mM KHCO3, 0.1 mM EDTA). MNCs were grown in serum-free media consisting of IMDM supplemented with 20% BIT (Stem Cell Technologies), 40 µg/ml low-density lipoprotein (Sigma-Aldrich), 10-6 M β-mercaptoethanol, and the following cytokines: 100 ng/ml SCF (Stem Cell Technologies), 100 ng/ml G-CSF, 20 ng/ml FLT3 ligand, 20 ng/ml IL-3, and 20 ng/ml IL-6 (Sigma-Aldrich). MNCs were grown at a density of $5\times10^5$ cells/ml at 37° C., 5% $CO_2$, overnight in a humidified incubator before drug treatment. The CML (K562) and AML (MOLM-14) cell lines were grown in suspension culture, in RPMI with 10% fetal bovine serum (Invitrogen), 1% L-glutamine (100 mM), and 1% penicillin/streptomycin (100 µg/ml), in a humidified incubator at 37° C., 5% $CO_2$.

K562 cells and MNCs were treated for 4 h with dasatinib, at a concentration of 100 nM unless otherwise specified. MOLM-14 cells were treated for 48 h with the following panel of FDA-approved kinase inhibitors, at $IC_{50}$ and $IC_{12.5}$: axitinib (100 nM, 25 nM), dasatinib (400 nM, 100 nM), erlotinib (7 µM, 1.75 µM), gefitinib (9 µM, 2.25 µM), pazopanib (2 µM, 0.5 µM)), imatinib (10 µM, 2.5 µM), ruxolitinib (10 µM, 2.5 µM), lapatinib (9 µM, 2.25 µM), nilotinib (9 µM, 2.25 µM), ibrutinib (1.6 µM, 0.4 µM), crizotinib (1.8 µM, 0.45 µM), ponatinib (4 nM, 1 nM), rapamycin (20 nM, 5 nM), sorafenib (8 nM, 2 nM), sunitinib (12 nM, 3 nM), and vandetanib (3.6 µM, 0.9 µM).

Immunoblotting analysis. K562 cell lysate was prepared by boiling cells in a SDS-PAGE loading buffer. Equivalents of $5\times10^5$ cells per untreated or dasatinib-treated conditions were subjected to SDS-PAGE and were immunoblotted with anti-pCRKL, anti-pSTAT5, anti-pSTAT3, and anti-pERK1/2 antibodies (Cell Signaling Technology) at 1:1000 in TBST overnight, after being blocked with 5% BSA in TBST. Phosphoprotein signal was imaged on a Lumi Imager.

Fluorescence-activated cell sorting (FACS) analysis. Untreated and kinase inhibitor-treated K562 cells were fixed and permeabilized according to the manufacturer's instructions (BD Biosciences); incubated with anti-pCRKL-PE, anti-pSTAT5-Alexa 488, anti-pSTAT3-PE, or anti-pERK1/2-Alexa 488 antibodies (all from BD Biosciences) for 1 hr in the dark; washed twice with PBS supplemented with 1% BSA; and analyzed on a FACS Aria instrument (BD Biosciences).

SC-QDP phosphoprotein labeling. Cells were fixed, permeabilized and dispersed onto cover glass chambers (Lab-Tek; Nunc), or custom-made, multi-well cover glass chambers for high throughput assays. The cells in each well were blocked and treated with primary anti-phosphoprotein antibodies (pCRKL, pSTAT5, pSTAT3, pERK1/2, pAKT473; Cell Signaling Technology). The anti-CD34 antibody (Dako, USA) was used for selection of CD34+ primitive cells. Following primary antibody incubation, cells were rinsed (by hand pipetting or by multichannel peristaltic pump) and treated with the following: secondary anti-IgG-QD or anti-IgG-Alexa 488, anti-mouse IgG-QD605, anti-rabbit IgG-QD-605, anti-mouse IgG, anti-rabbit IgG-QD-655, anti-mouse IgG-Alexa 488, and anti-rabbit IgG-Alexa 488 (Life Technologies). Concentrations of primary and secondary antibody probes were optimized for each anti-phosphoprotein marker to yield low background with isotype controls (2-3 and 6-7 QDs/cell in primary CML cells and AML cell lines, respectively). After cells were incubated with secondary antibodies, they were washed in buffer solution and imaged.

SC-QDP image acquisition. Cells were imaged with an inverted fluorescent microscope (Zeiss AxioObserver) equipped with high magnification objectives, QD filter sets (Semrock), and a Luca-R camera (Andor) suitable for detecting discrete QD fluorescence. Data acquisition consisted of acquiring multiple fields of view randomly for each well of the multi-well chamber. The microscope was controlled by Micromanager (www.micro-manager.org/) [31]. For each field of view, z-stacks of entire cells were acquired in appropriate QD fluorescent channels (inter-slice distances of 275-300 nm, total z-depth of 18 µm for K562 cells, and 10-12 µm for MOLM-14 cells and MNCs from patients) along with a differential interference contrast (DIC) image at mid-stack. Image acquisition was performed manually or by automated high-throughput scanning. For automated high-throughput scanning, a custom-written Java plugin for Micromanager was used that allows scanning of user-selected wells as well as random or user-selected areas within each well for DIC, and appropriate multiple quantum dot (QD) channels. The Java plugin also corrected slide tilt by determining the slide focal plane. Image focus at each well was verified and corrected manually if needed.

SC-QDP discrete QD counts in single cells. Levels of phosphoprotein activity were quantified in single cells using automated software imaging algorithms. Cell segmentation was first done manually and then was optimized for speed using an automated procedure. Automated cell segmentation comprised detecting the nucleus and plasma membrane using a threshold-based intensity algorithm and a membrane expansion cell segmentation algorithm (www.cellprofiler.org) of each cell [32]. Discrete QD fluorescence was detected, localized and tabulated on a per cell basis using automated algorithms written in MATLAB (Matlab). Briefly, detection of discrete QD probes was accomplished in single-cell z-stacks by applying a spatial bandpass filter, detecting localized maxima, and calculating the position of each QD for each z-slice. The QD localization precision was ~100 nm using centroid localization and ~20 nm using radial symmetry localization [33]. The output of these automated algorithms comprised total counts of detected and localized discrete QD fluorescent puncta in each single cell z-stack. QD counts represent the relative activity levels of a specific phosphoprotein, rather than the absolute count of all phosphoactivated proteins, as antibodies are full-length and may tag more than one activated phosphoprotein molecule. The QDs were identified as discrete, non-aggregated units comprised of single or a few QDs, as confirmed by intensity profile measurements of QD fluorescence [34,35]. Automated algorithms for counting discrete fluorescent QD-phosphoprotein complexes were validated by comparing to manual counting and showed a maximum difference of 3%.

Measurements of single-cell total fluorescence of QD and Alexa dyes were obtained for each cell by summing pixel values from all slices in a single z-stack corresponding to each cell and subtracting the global background value for each field of view from the image. The global background value was computed as the mean of the minimum pixel value corresponding to each y-column of the entire field of view in each image.

SC-QDP single-cell phosphoresponse profiles. Probability density estimate (PDE) plots were used to describe the frequency distribution of phosphoactivity levels of single cells sampled from the total cell population. The PDE plots represent an estimate of the underlying continuous probability density function and were computed with Gaussian kernel density estimation [36,37]. This estimation procedure is advantageous to histogram estimates as it provides a continuous estimate of the PDE and more rapidly converges to an estimated PDE, thereby requiring fewer sampled data points [38]. Moreover, Gaussian kernel density estimates are not biased by histogram bin width, bin number, or starting location of the bin; rather, the kernel width is dictated by computations of optimal Gaussian kernel bandwidths, assuming an underlying Gaussian distribution [39].

Results

Figure 1A:
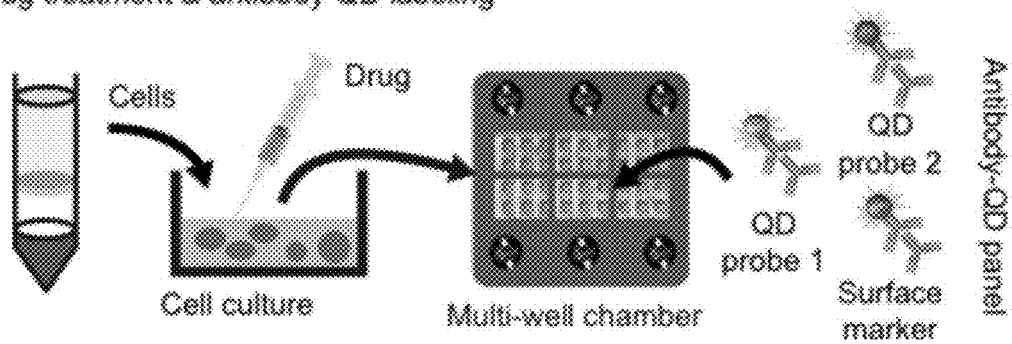
FIG. 1A shows the workflow of labeling cell culture with a label, for example, quantum dots. Cells are treated with kinase inhibitors, deposited on a multi-well cover glass chamber, and labeled with a panel of primary antibodies and multicolor secondary antibody-QD probes.
Figure 1B:
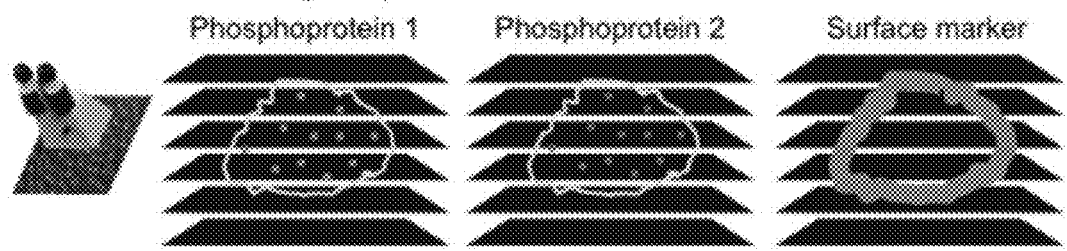
FIG. 1B shows the workflow of 3D multichannel image acquisition. Cell micrographs are acquired in separate fields of view for label detection in multichannel z-stacks.
Figure 1C:
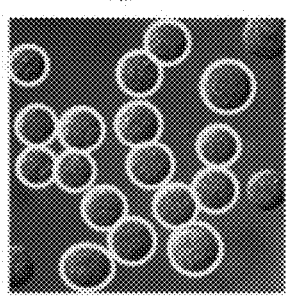
FIG. 1C shows the workflow of counting of discrete labels in single cells. Discrete QD labels are detected and counted in entire z-stacks and tabulated as the total for individual cells.
Figure 1C:
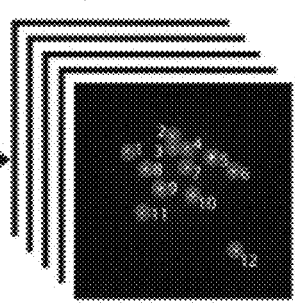
Figure 1C:
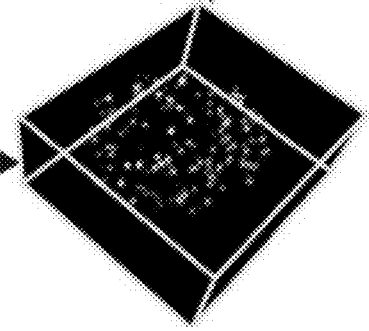
Figure 1D:
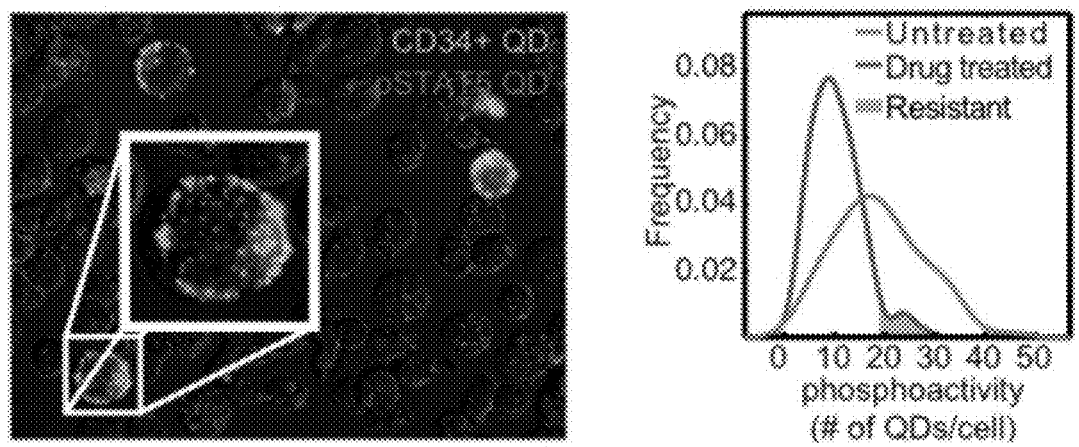
FIG. 1D shows the workflow of Single cell phosphoresponse profiling. Phosphoprotein QD counts for a single cell are profiled as probability density estimate plots with frequency of cells (y axis) as a function of phosphoactivity (x-axis) for untreated cells (green) and kinase inhibitor-treated cells (magenta).

Single cell quantum-dot phosphoassay platform (SC-QDP). The SC-QDP is a quantitative, ultrasensitive nanoparticle imaging assay comprising antibody-QD probe labeling and automated, high-throughput algorithms aimed at detecting the signaling activity levels of single cells by counting discrete complexes of activated phosphoprotein molecules. Cells are treated with a kinase inhibitor or another therapeutic of choice; deposited into multi-well, glass-bottom assay chambers; and then labeled sequentially with primary phosphoantibodies and secondary antibody-QDs (see FIG. 1A). This sequential labeling scheme allows the flexible pairing of any QD color with a phosphoprotein target. Moreover, the characteristic narrow fluorescence emission spectra of QDs allow for ease of QD multiplexing and simultaneous detection of single cell phosphoactivity with other cellular markers (e.g., nucleus, CD34+, etc.). SC-QDP phosphoprotein labeling produces a high level of post-assay cell retention compared with FACS (>95% versus 24-54%; see FIG. 2) and accommodates a relatively small number of cells (250-128,000 cells/well), thus overcoming constraints in the screening of limited sample sizes of primary cells from patients. SC-QDP image acquisition follows phosphoprotein labeling and involves automated multi-QD channel, z-stack acquisition of selected fields of view of phosphoantibody-QD labeled cells (see FIG. 1b). To measure single-cell phosphoactivity a new approach, leveraging the bright intensity and photostability of QDs was adopted to detect and tabulate the number of discrete QD-tagged phosphoprotein complexes in single cells using automated software algorithms (see FIG. 1c). Cellular debris and cell aggregates were automatically removed and the phosphoactivity measurement of each cell was visually compared to brightfield images to confirm that measurements were made of intact single cells. Probability density estimate (PDE) plots demonstrated the single cell kinase inhibitor responses based on the assessment of the underlying distribution of phosphoactivity levels. The PDEs show the mean and standard deviation ($\sigma$) of phosphoactivity levels for single cells sampled from the total cell population (see FIG. 1d).

Validation of the SC-QDP approach. To validate the nanoparticle-based SC-QDP approach, the results of SC-QDP were compared with those from immunoblotting and FACS assays in parallel experiments on the same set of cell samples. pCRKL, pSTAT5, and pSTAT3 were measured as surrogate markers of BCR-ABL1 kinase that is constitutively activated in human CML K562 cells.

Figure 3A:
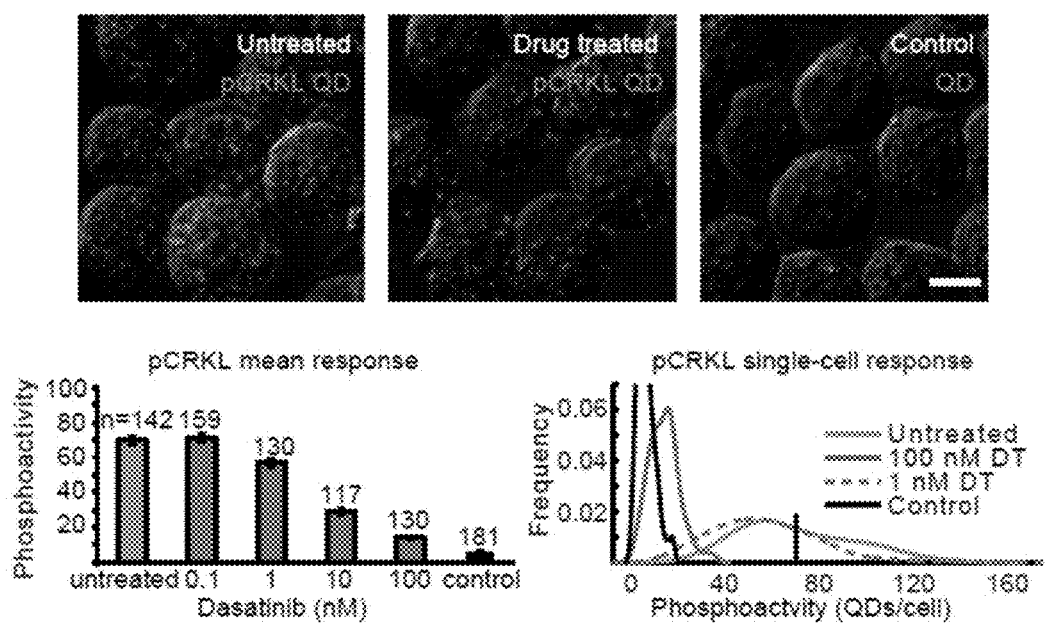
FIG. 3A is a set of three micrographs of CML K562 cells processed by SC-QDP for pCRKL in three conditions: untreated, dasatinib-treated (100 nM, 4 h), and no primary antibody (control). Images are collapsed z-stack overlays of pCRKL-QD (magenta) and brightfield DIC channels. Scale bar is 10 ⎕ m. Bar graphs show the mean pCRKL activity (y axis), computed as the average number of discrete QD counts for each K562 cell at each dasatinib concentration (x axis). Error bars are standard error of the mean. n is the number of cells sampled. PDE plots represent the single cell phosphoactivity data showing the frequency of single cells (y axis) as a function of phosphoactivity (# of QDs per cell, x-axis) in untreated (green), dasatinib-treated (magenta), and no primary antibody (control; black) K562 cells. Vertical black line is the mean phosphoactivity of untreated K562 cells.
Figure 4A:
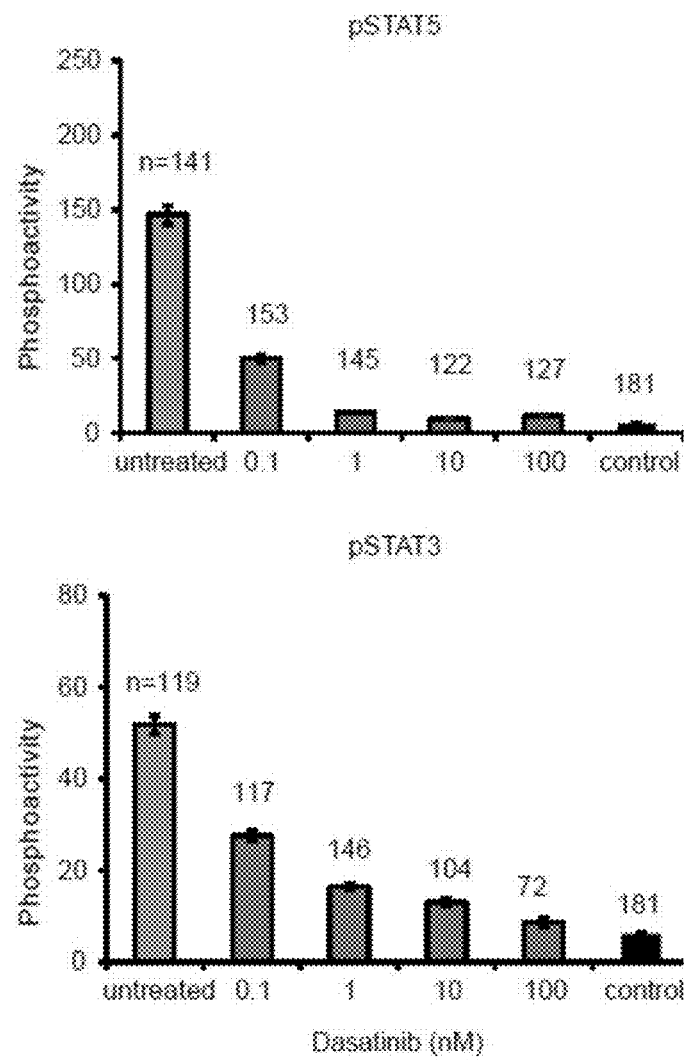
FIG. 4A is a set of two bar graphs that show the mean phosphoactivity (y axis), as measured by the average of discrete QD counts, and computed from single K562 cells for each dasatinib drug dose (x axis). Error bars are standard error of the mean. n is the number of cells sampled.
Figure 4B:
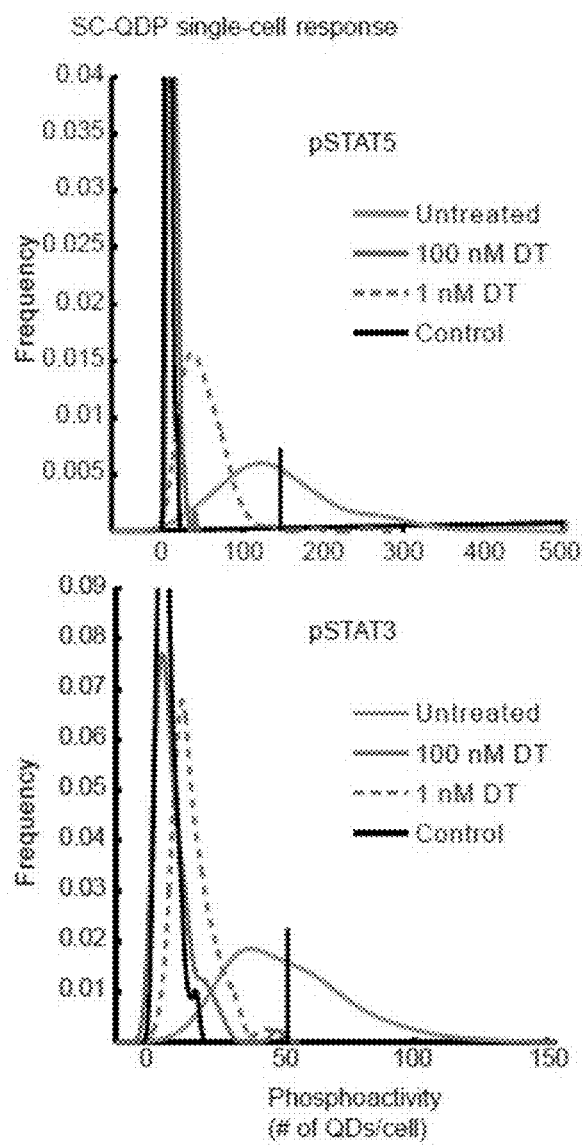
FIG. 4B is a plot of single cell phosphoactivity represented by probability density estimate (PDE) plots. PDE plots show the frequency of single cells (y axis) as a function of phosphoactivity (# of QDs per cell, x-axis) in untreated (green), drug-treated (magenta), and control with no primary phosphoantibody omitted (black) in K562 cells. Vertical black lines are the mean phosphoactivity of untreated K562 cells.

SC-QDP analysis showed that untreated CML K562 cells express high basal levels of QD-pCRKL activity that are reduced with dasatinib treatment (FIG. 3a). Negative control experiments performed by omitting primary phosphoantibody staining showed only a few QDs per single cell, indicating low non-specific binding (control, FIG. 3a). Single-cell phosphoprotein levels were quantified by tabulating discrete QD counts for each cell (pCRKL, FIG. 3a; pSTAT3, pSTAT5, FIG. 4a). Bar graphs depicting the average single cell phosphoactivity level revealed a trend of decreasing phosphoactivity with increasing concentration of dasatinib for all three phosphoprotein targets (pCRKL, FIG. 3a; pSTAT3, pSTAT5, FIG. 4a). These bar graphs also quantitatively revealed that the SC-QDP assay provides an excellent signal-to-noise (S/N) ratio for all three phosphoprotein probes, as controls omitting the primary phosphoantibody showed negligible levels of non-specifically bound QDs (6-7 QDs/cell on average; FIG. 3a and FIG. 4a). Negligible levels of non-specific binding were also reflected by the low numbers of QDs per cell in the presence of dasatinib (100 nM), which largely suppressed phosphoactivity (FIG. 3a and FIG. 4a). PDE plots of single-cell phosphoresponses showed that dasatinib treatment shifted and narrowed the PDE curve (solid green and dotted magenta curves versus solid magenta curves; FIG. 3a and FIG. 4b), indicating a mean phosphoinhibition and reduction of phosphoheterogeneity that are consistent with qualitative cell image data. The width of the PDE plots demonstrated that CML K562 cells exhibit considerable phosphoheterogeneity at baseline, which decreased with increased dasatinib concentration for all three phosphoprotein species, pCRKL, pSTAT5, and pSTAT3 (FIG. 3a and FIG. 4b). Variations in cell division contributed to this heterogeneity, as lovastatin-induced cell cycle synchronization reduced this heterogeneity (data not shown).

Figure 3B:
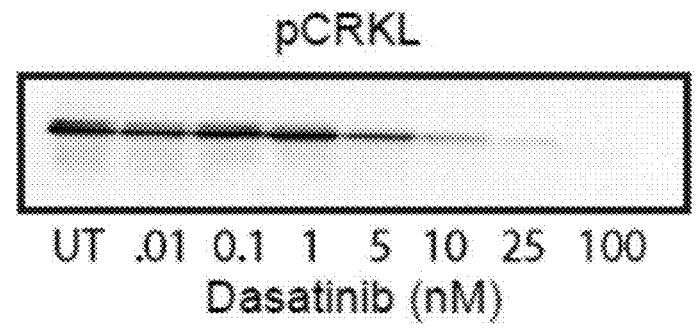
FIG. 3B is an image of an immunoblot showing pCRKL levels in K562 cells treated with increasing concentrations of dasatinib. UT=untreated.
Figure 3C:
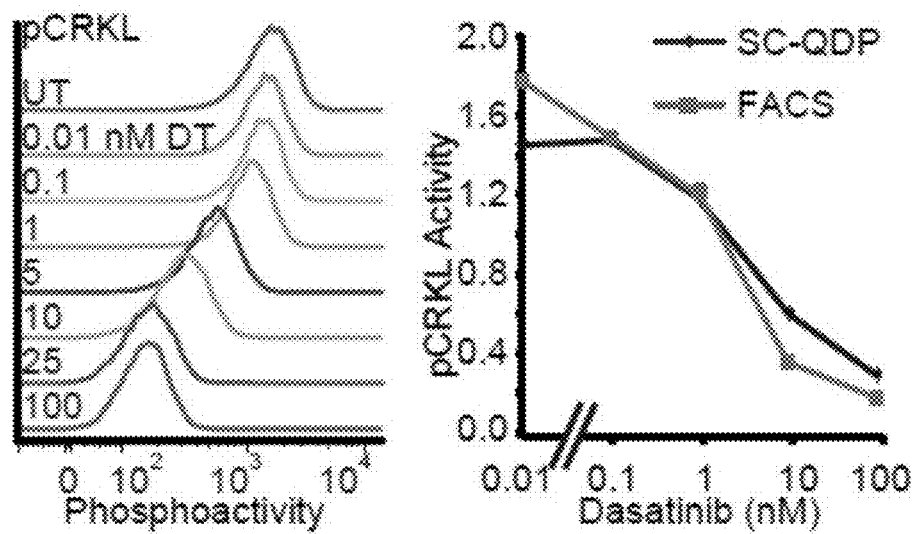
FIG. 3C is a set of two FACS histograms. The left panel shows pCRKL levels in K562 cells treated with increasing concentrations of dasatinib (DT). UT=untreated. Line plots (right panel) compare phosphoactivity (y axis) measured by SC-QDP (blue) and FACS (magenta). Phosphoactivity value represents the normalized mean of five different sampled points.
Figure 4C:
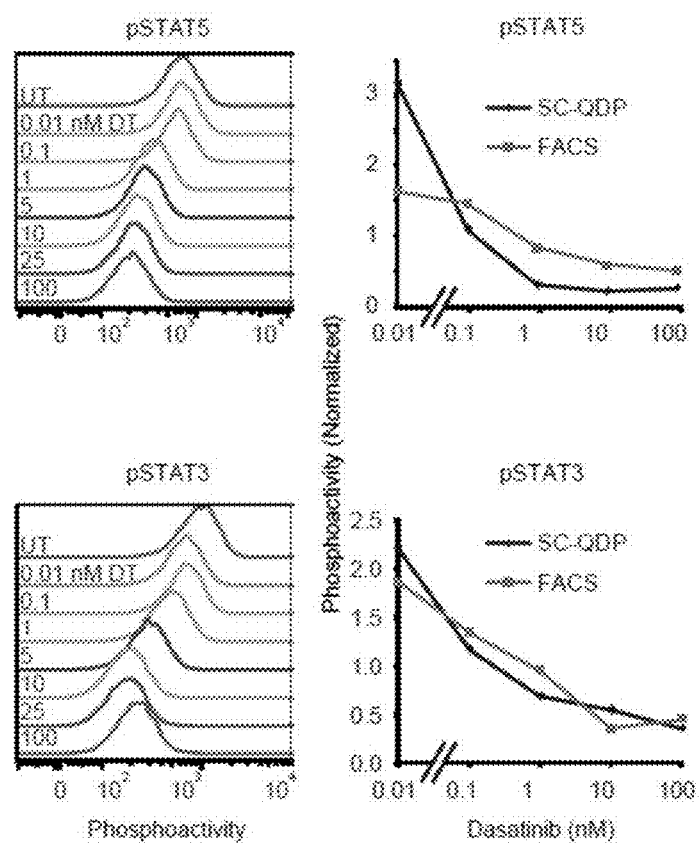
FIG. 4C is a set of FACS histograms showing pSTAT5 and pSTAT3 levels in K562 cells treated with dasatinib (DT) in increasing concentrations; UT=untreated. Line plots (right) compare phosphoactivity (y axis) as measured by SC-QDP assays (blue) and FACS (magenta). Phosphoactivity value at each point is normalized to the mean of all five points in the plot.
Figure 4D:
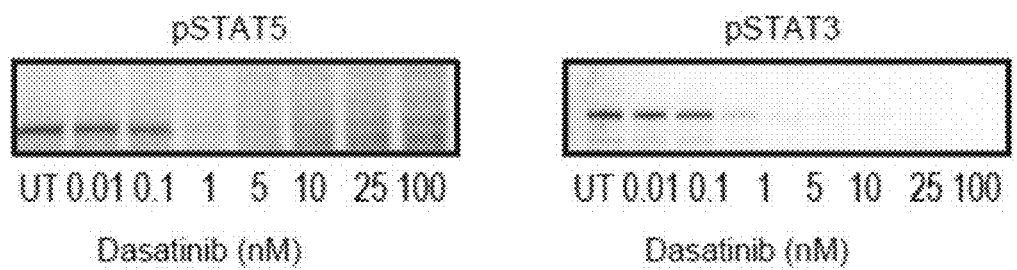
FIG. 4D is a plot of immunoblots showing Immunoblots show pSTAT5 and pSTAT3 levels in K562 cells treated with dasatinib in increasing concentrations.

SC-QDP results were similar to immunoblotting and FACS analyses. SC-QDP and immunoblot assays both showed decreasing phosphoactivity with increasing dasatinib concentrations. In particular, SC-QDP and immunoblots both showed a sharp dasatinib-induced inhibition of pSTAT5 (FIG. 3b) and a gradual inhibition of pSTAT3 and pCRKL (FIG. 4d). SC-QDP and FACS analyses revealed decreases in mean phosphoactivity levels with greater dasatinib concentrations in qualitative and quantitative comparisons (FIG. 3c and FIG. 4c). Thus, the SC-QDP method was found to be consistent with standard immunoblotting and FACS assays, establishing the validity of the SC-QDP approach for quantifying phosphoprotein activity by counting discrete fluorescent probes.

Figure 5A:
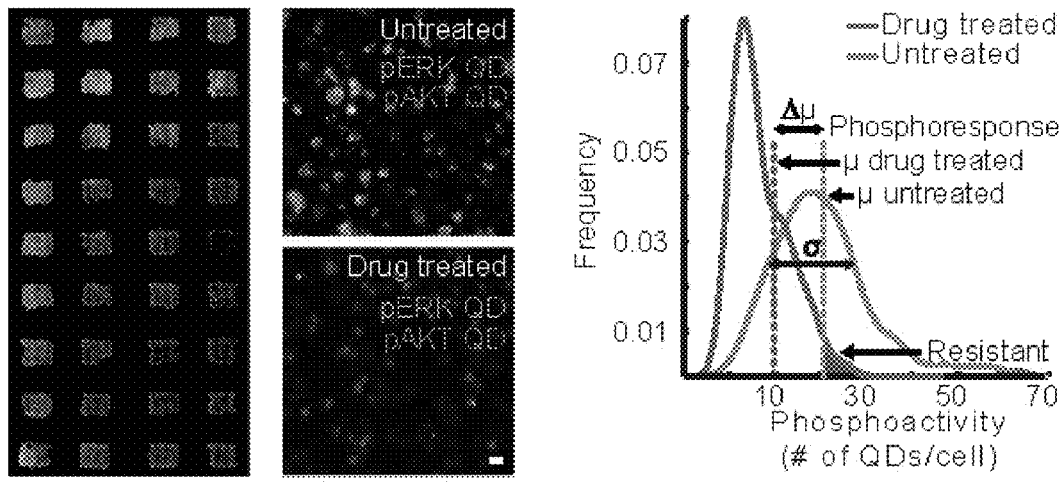
FIG. 5A is an example of image data from high-throughput SC-QDP kinase inhibitor screening. Left panel: fluorescence image of human MOLM-14 AML cells in a 36-well chamber. Middle panel: representative images of QD-pAKT- (magenta) and QD-pERK- (green) labeled cells in untreated and inhibitor-treated conditions (vandetanib, IC50). Cell nuclei stained in blue, scale bar is 10 ⊡ m. Right panel: graph depicting values measured in subsequent plots.
Figure 5B:
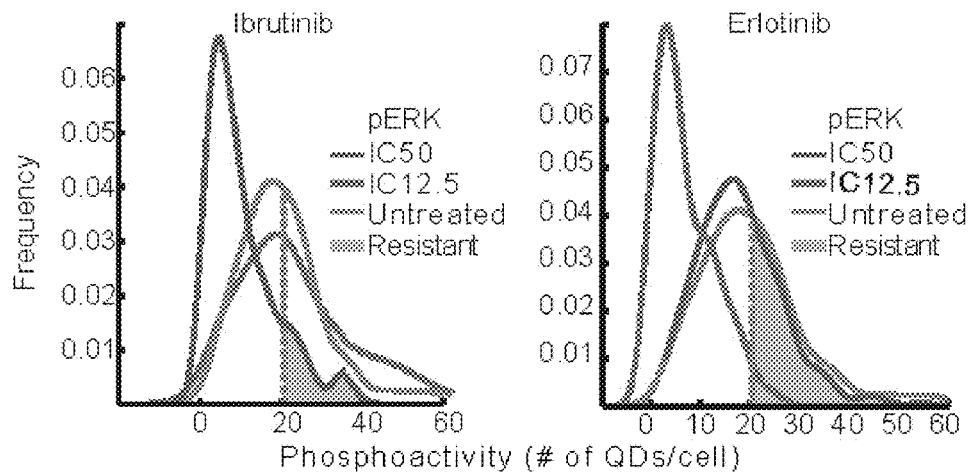
FIG. 5B is a set of two representative PDE plots of pERK activity following ibrutinib or erlotinib treatment show heterogeneity in inhibition levels of pERK at IC50 and IC12.5. Dotted green line is mean pERK level of untreated cells. Purple shaded area represents proportion of resistant cells (percentages shown in FIG. 5C).
Figure 5C:
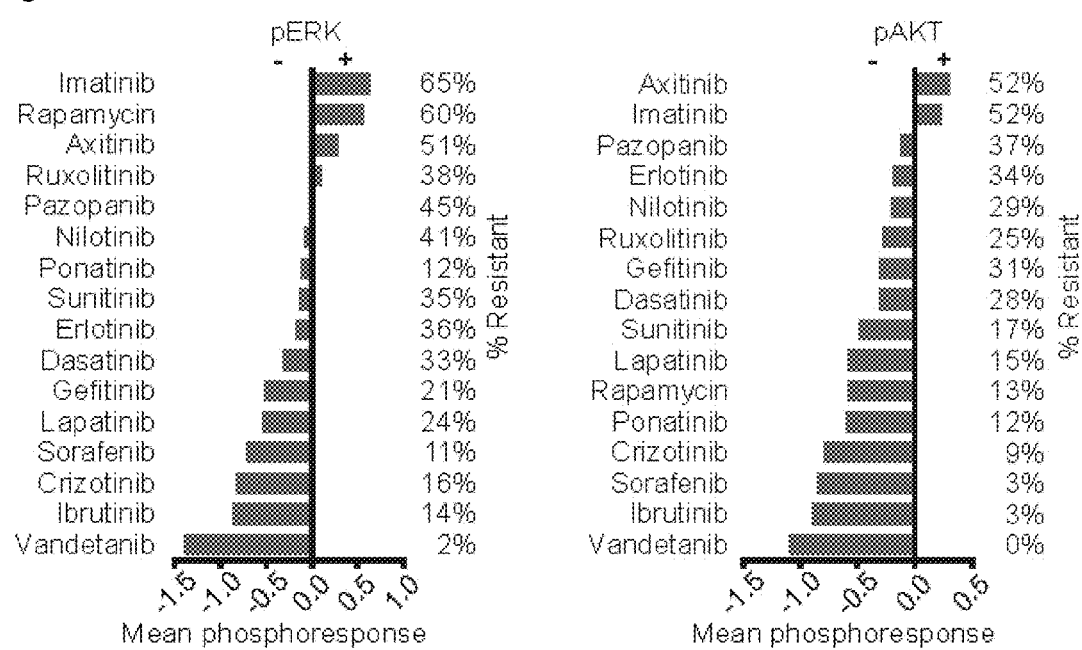
FIG. 5C is a graph showing the results of a kinase inhibitor panel, ranked in order of increasing mean pAKT and pERK inhibition in MOLM-14 AML cells (at $IC_{50}$ concentration). Bars show proportion of pAKT and pERK inhibition and, in some cases, activation (bars left and right of vertical line, respectively). Amount of inhibition/activation is defined as the mean phosphoresponse and is calculated as the difference between the inhibitor-treated mean and the untreated mean, in units of standard deviation ($\mu$) of the untreated cells. The percentage of resistant cells is defined as the proportion of inhibitor-insensitive cells that have phosphoactivity higher than the mean of untreated cells. Number of MOLM-14 cells sampled is n=205 (+/−54) per condition.

SC-QDP molecular counting method provides ultrasensitive phosphodetection. The SC-QDP approach of counting discrete QD-tagged phosphoproteins produced a substantial improvement in phosphodetection sensitivity over methods that quantify total fluorescence (e.g., FACS, standard immunocytochemistry). A comparison of phosphoactivity quantification by QD counting versus QD total fluorescence showed that QD counting resulted in a markedly higher S/N ratio (FIG. 5a). pCRKL activity measured in untreated CML K562 cells by QD counting showed an S/N ratio of 11.4 at baseline, compared to 4.7 and 2.3 in dasatinib-treated cells (10 nM and 100 nM, respectively). By comparison, QD total fluorescence showed S/N ratios of 1.1 and 1.7 for untreated and dasatinib-treated cells. Furthermore, comparative evaluation of cell phosphodetection sensitivity by QD counting versus QD total fluorescence and Alexa 488 total fluorescence revealed that the discrete QD-count method yielded the best S/N ratio for four additional phosphoproteins (pSTAT5, pSTAT3, pERK, and pAKT, FIG. 5b). Care was taken in these comparisons to use the same primary phosphoantibodies in both QD and Alexa dye labeling, and to optimize the concentrations of each primary phosphoantibody separately for QD and Alexa conditions. These experiments were performed in highly abundant phosphoprotein conditions, that is, in CML K562 cells and without kinase inhibitor treatment. Yet for all phosphotargets, the S/N ratio of Alexa dyes was often close to the background noise floor (S/N=1.6-3.8), whereas the QD counts provided significantly higher detection sensitivity (S/N=2.4-9.4). This increased level of phosphodetection sensitivity using SC-QDP discrete counting becomes particularly important because phosphoactivity is substantially reduced by treatment with kinase inhibitors, conditions under which differentiating single cell phosphoprotein levels from assay noise is technically challenging (FIGS. 5c and 5d, dotted line). Taken together, these data demonstrate that SC-QDP discrete probe counting of activated phosphoproteins provides substantial improvement in single-cell phosphodetection sensitivity that is particularly critical for single-cell measurements of kinase inhibitor efficacy.

Figure 6A:
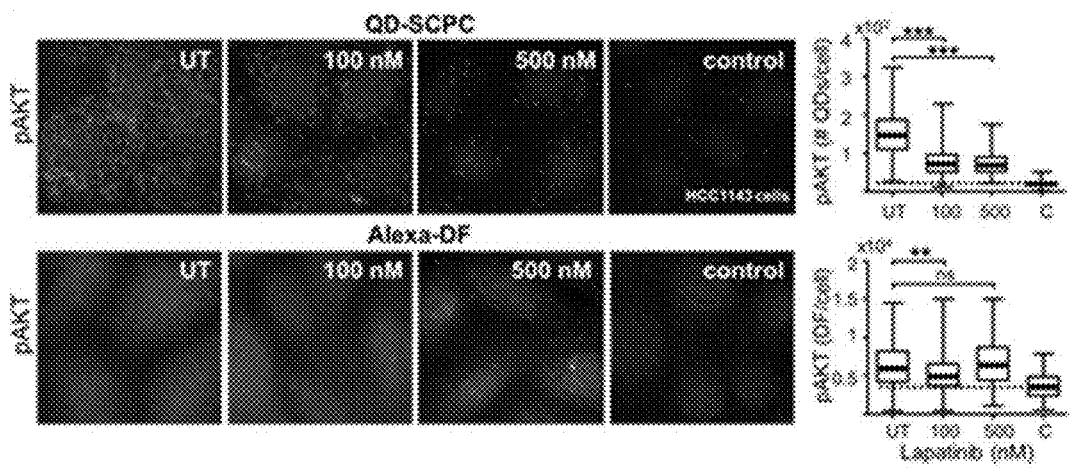
FIG. 6A is a set of raw images of HCC1143 cells exposed to the indicated concentration of lapatinib KI in. Boxplots show improved discrimination of pAKT for at higher KI doses by QD-SCPC vs. total diffuse Alexa488 fluorescence/cell. Identical primary PP-antibody was used and separately optimized for QD and Alexa488 labeling. Control (isotype primary Ab; dashed line, boxplots) shows background noise level.
Figure 6B:
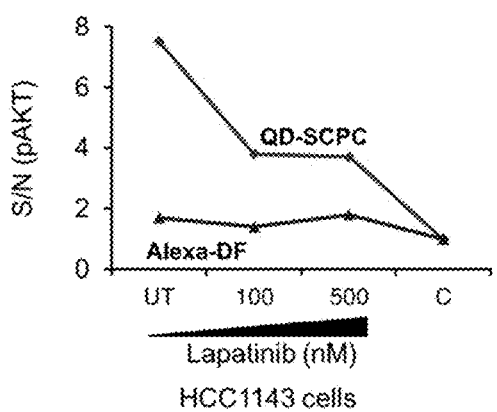
FIG. 6B is a plot showing that statistically significant resolution of pAKT levels is possible by SCPC vs. Alexa diffuse fluorescence. S/N ratio computed from boxplot data in FIG. 6A.
Figure 6C:
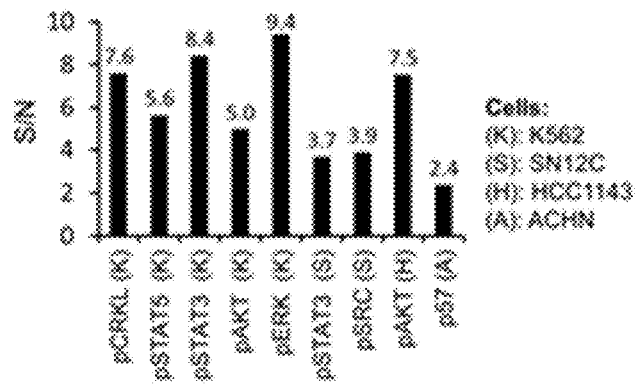
FIG. 6C is a bar graph showing High S/N ratios achieved for a variety of key QD-anti-PP probes in different cell systems (leukemia, breast cancer, kidney). Signal is the mean PP-response and background noise is the mean PP=level of the control (primary Ab isotype substituted for primary PP Ab).

SC-QDP reveals that phosphoinhibition heterogeneity and resistance is common at the single-cell level despite potent inhibition in the total cell population. The single-cell phosphoprofiling capabilities of the SC-QDP were tested by applying it to acute myeloid leukemia MOLM-14 cells exposed to a multi-drug panel of FDA-approved kinase inhibitors (FIG. 6a). The results not only showed feasibility, but also the value of SC-QDP measurements to capture important new single-cell signaling behavior that would otherwise be masked by averaged phosphoactivity information. SC-QDP measurements of pERK and pAKT showed that while a kinase inhibitor may exert an overall high inhibitory response (e.g. ibrutinib and erlotinib evoked a left-shift in pERK and pAKT, FIG. 6b and FIG. 7, respectively), there exists, among individual cells, a broad heterogeneity in pERK and pAKT activity in response to therapeutic inhibition. A broad heterogeneity in kinase inhibitor sensitivity was also observed for pAKT in these same cells (shaded area, FIG. 7). Moreover, this broad heterogeneity included individual cells that exhibited very high levels of phosphoactivity, and thus possessed high levels of phospho-inhibitor drug resistance. For example, 14% and 36% of cells were resistant to ibrutinib and erlotinib, respectively, as defined by pERK levels that are equal to or greater than the mean level of pERK in untreated cells (shaded area, FIG. 6b). FIG. 6c shows a ranking of kinase inhibitor responses by increasing order of mean pERK and pAKT inhibition and shows that as evaluated by averaged pERK and pAKT inhibition, it appears that many kinase inhibitors exert a potent inhibitory effect on cell populations. Yet, when phosphoresponses are examined with single cell granularity, the efficacy of phosphoinhibition is only partial; a high proportion of cells remain insensitive to phosphoinhibition (2-41% for pERK, and 3-37% for pAKT, FIG. 6c). Moreover, the ultrasensitive capability of the SC-QDP for kinase inhibitor screening revealed a rarely-reported phenomenon in which some kinase inhibitors produce phosphoinhibition of pERK and pAKT at a low $IC_{12.5}$, but produced phosphoactivation of pERK and pAKT at a higher $IC_{50}$ concentration (e.g. see erlotinib for pERK and pAKT, FIG. 6b and FIG. 7a, respectively).

Overall these findings demonstrate that the SC-QDP is capable of sensitively differentiating among phosphoresponse levels in single cells in a multi-panel kinase inhibitor screening to capture important, detailed cellular signaling information in single cells that is otherwise masked using by phosphoresponse averaging.

Chronic myeloid leukemia patients harbor rare CD34+ cells with high drug resistance. The identification of kinase inhibitor resistance in rare primitive cell populations from primary leukemia patient samples by direct phosphoresponse measurement has been challenging to routinely accomplish using standard immunoblotting and FACS methods [12]. The clinical capability of the SC-QDP for identifying rare kinase inhibitor insensitive cells was tested by assaying single CD34+ cells obtained from CML patients. SC-QDP analysis was performed on peripheral and bone marrow-derived mononuclear cells (MNCs) from 5 patients with newly diagnosed CML. These CML patients exhibited high leukemic cell burden with 85-99% of cells positive for BCR-ABL1 by cytogenetics. Consistent with the chronic phase of disease at diagnosis, the specimens from these patients exhibited low levels of blasts (1-4%) (FIG. 8a). MNCs from these patients were treated with the potent BCR-ABL1 kinase inhibitor, dasatinib (100 nM, 4 h), and SC-QDP was then used to measure the levels of pCRKL and pSTAT5, both of which are critical BCR-ABL1 downstream signaling mediators, in single CD34+ cells [8,23,24].

Figure 8C:
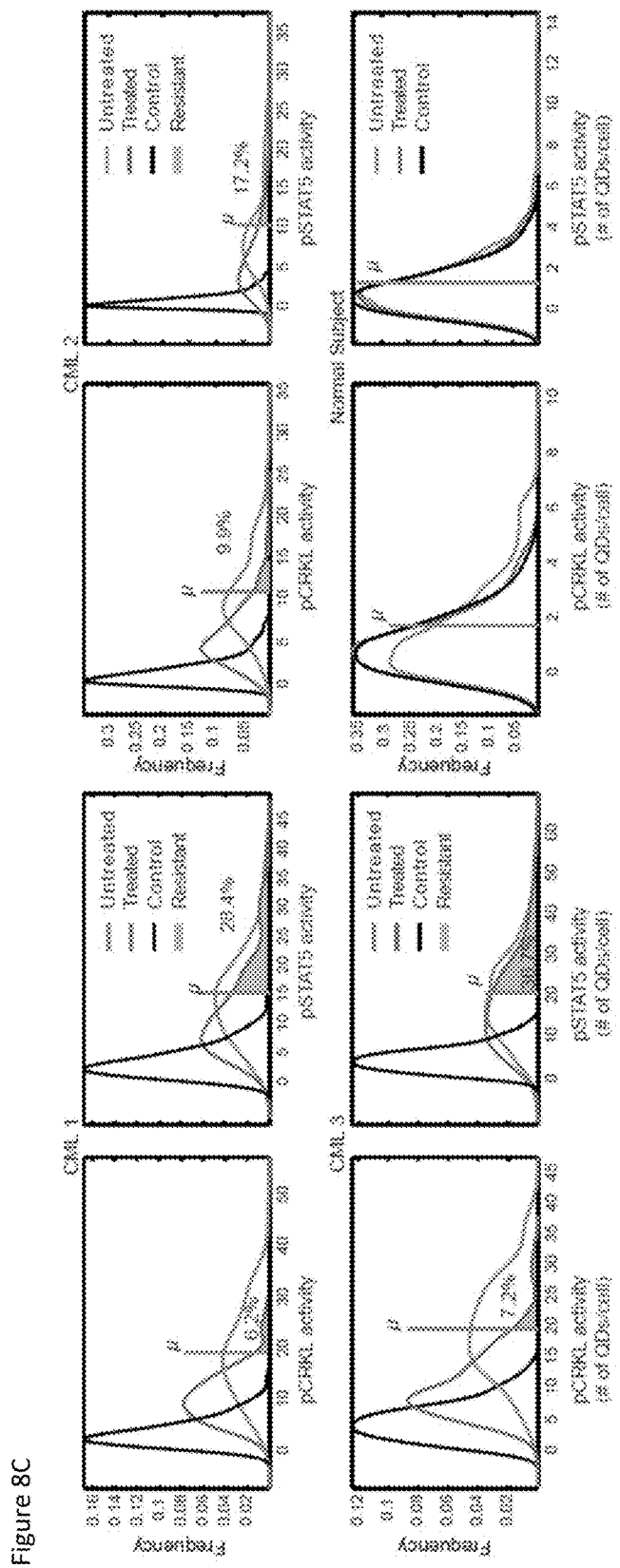
FIG. 8C is a set of eight plots showing PDE (probability density estimate) plots of pCRKL and pSTAT5 profiles of CD34+ cells from CML patients (n=3) and MNCs from healthy subject (n=1). Cells were treated with 100 nM dasatinib for 4 h. Mean phosphoactivity level ($\mu$) of untreated cells is marked by a vertical green line. The proportion of the inhibitor-treated cells with phosphoactivity levels above the mean value (right of $\mu$) is shaded, and the percentage of dasatinib-resistant cells is given. PDE curve of the isotype control represents assay noise (black curve). The number of CD34+ cells sampled for the measurement of pCRKL activity for the three patients was: 80, 87; 195, 196; and 160, 191, for untreated and inhibitor-treated conditions, respectively. The number of CD34+ cells sampled for the measurement of pSTAT5 activity for the three patients was 82, 91; 179, 190; and 177, 159, for untreated and inhibitor-treated conditions, respectively. The numbers of MNCs sampled from the healthy subject for measurements of pCRKL and pSTAT5 activity was n=179-196 and n=170-300, for untreated and control isotype, respectively.

FIG. 8b shows heterogeneous combinations of single-cell CD34 positivity and pCRKL expression in untreated MNCs from a CML patient. SC-QDP indicated a 1-4% CD34+ cell frequency range in the five CML patients. Quantitative SC-QDP analysis showed that, at baseline, there existed a wide-ranging level of heterogeneity of single CD34+ cell pCRKL activity (green curve of PDE plots for three patients, FIG. 8C; two patients, FIG. 9). For all five patients, dasatinib treatment induced a significant pCRKL inhibition (~1.8-fold shift in peak of magenta curve to left of vertical dashed line, FIG. 8C and FIG. 9) and a reduction in pCRKL expression heterogeneity (narrowed width of magenta curve, FIG. 8C, FIG. 9). However, SC-QDP analysis also showed, in all five patients, that a subpopulation of CD34+ cells retained high levels of pCRKL following dasatinib treatment (shaded magenta area, FIG. 8C and FIG. 9). The frequency of dasatinib-resistant CD34+ cells was 5.4-9.9% of the total dasatinib-treated cell population. The resistant cells were defined as those expressing pCRKL levels equal to or greater than the mean pCRKL activity level of untreated CD34+ cells. An alternative definition for the threshold of resistance that is based on the mean and standard deviation ($\sigma$) of the untreated CD34+ population (CD34+ cells that express pCRKL levels greater than mean$_{untreated}$−0.5$\sigma_{untreated}$), yielded even higher values for the frequency of dasatinib-resistant CD34+ cells (8.5-53.9%).

The reliability of estimates of the frequency of resistant cells identified by SC-QDP was demonstrated as follows. First, an independent computation was performed in which the frequency of cells with pCRKL levels above threshold was directly calculated by examining pCRKL levels for each cell and comparing this to estimates derived from PDE plots. Second, visual inspection of cells identified as resistant were confirmed as single and intact (i.e., not debris or doublets). Third, it was found that dasatinib-treated CD34+ cells showed levels of pCRKL that were higher than those determined by isotype control experiments (FIG. 8C and FIG. 7). Finally, while samples collected from healthy subjects did not show significant levels of CD34+ cells, SC-QDP analysis performed on CD34− cells from the MNCs of a healthy subject showed pCRKL levels that were similar to assay noise both in dasatinib-treated and untreated conditions. These cells had mean pCRKL levels 5-8 times lower than the pCRKL levels in CD34+ cells from the CML patients (FIG. 8c). These data demonstrate the ultrasensitive ability of the SC-QDP to clearly identify dasatinib-sensitive and dasatinib-resistant CD34+ cells within patient samples.

The SC-QDP's readily expandable panel of markers facilitated identification of resistant cells in these same five patients using pSTAT5, an alternative surrogate marker of BCR-ABL1 activity [8,23,24]. SC-QDP showed a mean reduction of pSTAT5 following dasatinib treatment (FIG. 6C, FIG. 9) consistent with BCR-ABL1 inhibitor treatment of CD34+ patient cells. In contrast, pSTAT5 expression levels in healthy subject MNCs were close to assay noise in dasatinib-treated and untreated conditions (FIG. 8c). SC-QDP analysis using pSTAT5 as a biomarker revealed resistant CD34+ cells (FIG. 6C and FIG. 9), which was similar to the finding for pCRKL. The detected resistant CD34+ cell population comprised 17-37% of MNCs in the five patients, as defined by a threshold in which pSTAT5 activity was greater than the mean pSTAT5 activity of untreated CD34+ cells. These measurements show that the SC-QDP capabilities overcomes technical challenges that have otherwise made the identification of primary patient CD34+ cells that are pSTAT5 resistant difficult by methods such as immunoblotting and FACS [10,12]. The ultrasensitivity of the SC-QDP to directly profile specific phosphorylation state was also highlighted in the data in which the use of pSTAT5, compared to pCRKL as a biomarker, identified a higher percentage of resistant cells; in contrast, past immunoblotting studies have used pCRKL and pSTAT5 interchangeably as biomarkers of BCRL-ABL1 signaling [10,12]. This new information strongly suggests that other signaling pathways also activate STAT5 phosphorylation [24], and that results of measurements of single-cell resistance may be dependent on the choice of the phosphofunctional marker. Overall, these data demonstrate the clinical value of using the SC-QDP to sensitively identify and directly phosphoprofile rare subpopulations of kinase inhibitor-resistant cells from primary patient cell samples. Previous approaches have not provided such direct phosphorylation-based identification of cellular phosphoresistance [10,12].

These examples demonstrate the disclosed approach for the ultrasensitive quantification of proteins in single cells by counting discrete nanoparticle quantum dot-tagged protein complexes. This molecular counting approach achieves a detection sensitivity that supersedes conventional fluorescence measurements (FIG. 5), as it is less susceptible to errors arising from variations in the intensity of individual fluorescent emitters and other diffuse fluorescent noise sources (e.g. cell autofluorescence). Given that levels of signaling protein molecules can be present in low abundance in single cells [1-3], and that such levels are often reduced further by therapeutic compounds, this molecular approach is of broad value for quantifying not only cellular signaling molecules but a variety of other molecules at limited abundance in single cells (e.g. ligands, surface markers, viral particles).

The implementation of this ultrasensitive protein counting approach by SC-QDP was demonstrated in two applications in which: 1) single acute myeloid leukemia MOLM414 cell responses to a panel of commonly investigated kinase inhibitors were phosphoprofiled, and 2) single CD34+ stem cells obtained from chronic myelogenous leukemia patient cells were phosphoprofiled. These example applications not only demonstrated the capabilities of the disclosed approach but also revealed phosphoresponse differences amongst single cancer cells that point to the significant value of the disclosed methods. In particular, it was found that many common kinase inhibitors exert potent inhibition in the overall leukemic cell population, but drug-resistant cells expressing high levels of pERK and pAKT signaling are prevalent (FIG. 6). Additionally, the high potential value of using the SC-QDP to identify rare CD34+ cells that are resistant to the highly potent BCR-ABL1 kinase inhibitor, dasatinib was demonstrated. While the existence of dasatinib-resistant cells has been identified by genomic and cell proliferation studies [12,18], technical limitations in immunoblotting and FACS methods have impeded the direct identification of phosphoactivity in rare subpopulations of dasatinib-resistant cells [12]. Interestingly, while the frequency of dasatinib-resistant CD34+ cells was relatively low (FIG. 8C and FIG. 9), all 5 CML patients sampled harbored resistant cells possessing high levels of phosphoinhibition suggesting incomplete inhibition of BCR-ABL gene, or downstream phosphoprotein target activity as the key reason for CML persistence. These results indicate that single-cell metrics are needed to comprehensively assess the degree of effectiveness of drug response. Such information would be of high biomedical value for enabling further investigation into cellular heterogeneity and its role in disease persistence [25,26,27].

Figure 2A:
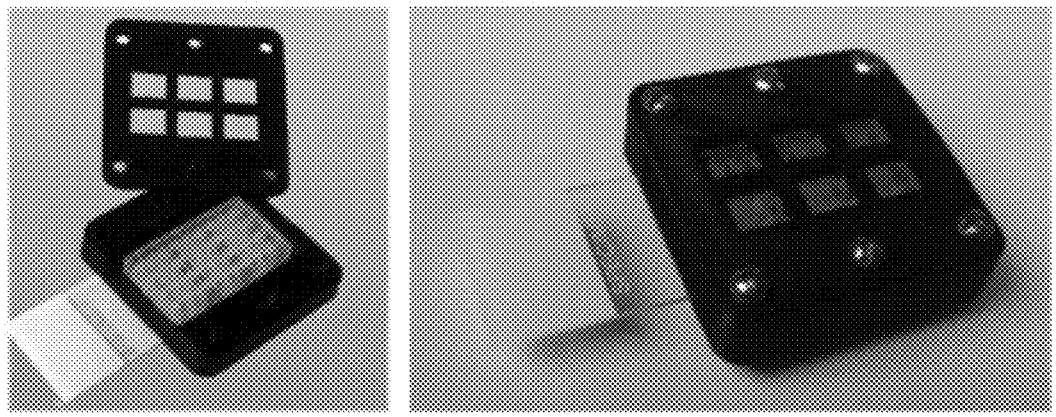
FIG. 2A shows the components (left) and the assembly (right) of a SC-QDP multi-well glass chamber. Multi-well chambers use low volumes of reagent (10-20 µl/well, 36-60 wells) and are used for both phosphoprotein labeling and imaging.
Figure 2B:
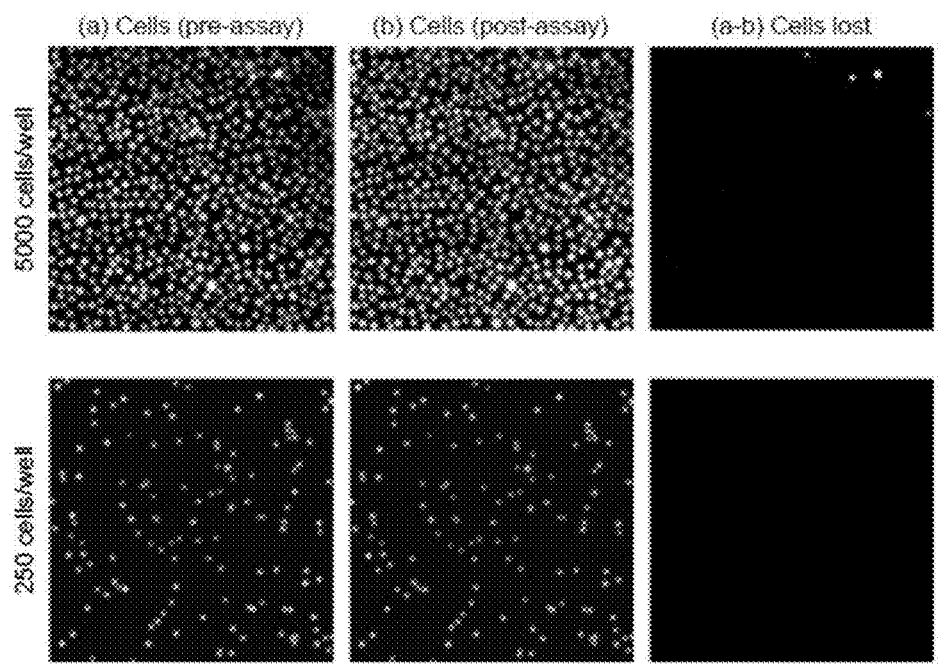
FIG. 2B is a set of six images of probe labeling in multi-well chamber showing high cell retention that enables handling of samples with limited numbers of cells. Example micrographs of CML K562 cells before and after SC-QDP probe labeling show very few cells lost after the assay, even for small numbers of cells (250 and 5,000 cells/well). Each micrograph is a composite of 25 fields of view from one well. Cells are labeled with CellMask.
Figure 2C:
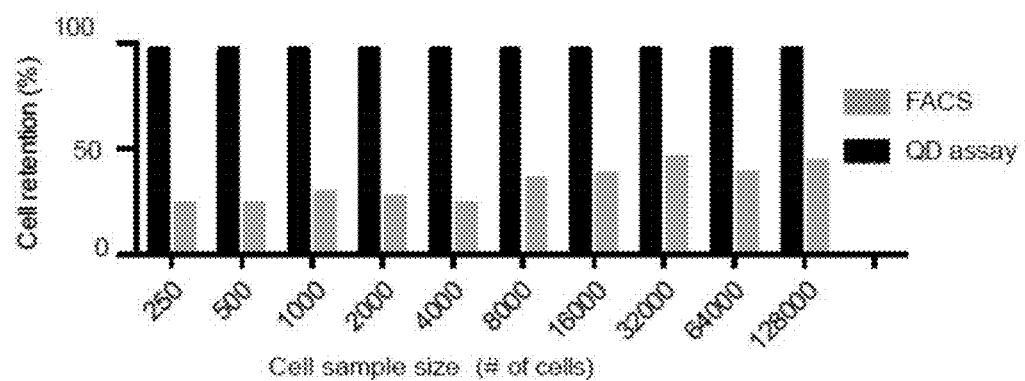
FIG. 2C is a graph of a quantitative comparison of cell retention after SC-QDP and FACS processing of identical CML K562 cell samples shows higher cell retention (>95-99%) with SC-QDP compared to FACS (24%-53%) for a broad range of cell numbers (250-128,000). Plots are the percentage of cells retained as a function of the initial number of cells per sample.

The SC-QDP is an integrated, automated imaging-based microscope platform that incorporates additional advantageous features to provide combined capabilities not available in current standard proteomic assays. The imaging-based nature of the SC-QDP offers the capability to visually discern single cells from artifact (e.g. debris, aggregates). This automated feature is useful for accurate identification of rare cellular subpopulations. The imaging-based nature of the SC-QDP also offers potential for the spatial analysis of proteins in intact, single cells, a capability that is not possible with cell destructive methods such as FACs and mass spectrometry. Another valuable feature of the SC-QDP is its capability to accommodate small samples of limited cell number with minimal cell loss (<5% cell loss at 250-128,000 cells, compared to 46-75% cell loss in FACS (FIG. 2). This format of single cell profiling of miniaturized sized samples opens up opportunities which are not practical by FACS and mass spectrometry approaches [12], such as performing single cell proteomic profiling on samples of limited size (e.g. limited patient samples), and under multiple conditions (e.g. multi-drug panels, combinatorial drug screening). Overall, perhaps the most powerful implementation of the SC-QDP would be its use with FACS, mass spectrometry, and other new cell electrochemical methods in order to provide complementary, comprehensive single-cell proteomic information [28-30].

In summary, the systems and methods of discrete counting of nanoparticle-tagged proteins described herein have broad relevance for investigators seeking to quantify proteins of low abundance in single cells. Application of these approaches would allow investigators to perform single cell proteomic profiling of a wide variety of cellular proteins. This capability opens up new opportunities for studies aimed at understanding the role of cellular signaling heterogeneity in disease such as cancer. Moreover, this nanoparticle-tagged protein counting methodology and its implementation by SC-QDP is a potentially powerful tool for evaluating drug response, discovering and developing new treatment strategies, particularly when coupled with other proteomic and next-generation, single-cell sequencing approaches.

FIG. 10 shows an embodiment of a system 1000 for automated detection and counting of biomolecules. The system 1000 can include a microscope 1002, a computer 1004, a camera 1006, and an automated stage 1008. The microscope 1002 can include one or more microscope objectives 1010, one or more filter cubes 1012 and a light source 1014. A sample 1016 containing the biomolecules (e.g., proteins) to be counted may be placed on the automated stage 1008. The sample 1016 can be in a variety of formats e.g., a protein microarray, which uses a glass slide containing molecules of protein affixed at separate locations in an ordered manner to form a microscopic array. In any event, it is desirable that the base material upon which the biomolecules are affixed or positioned is transparent.

The computer 1004 is coupled to the camera 1006, the stage 1008, the objectives 1010, the filter cubes 1012, and the light source 1014 as shown by connections 1020, which may be established through electrical cables or wireless communication. In operation, the user turns on the light source 1014, which emits an excitation light 1022. The excitation light 1022 is at a first wavelength and encounters filter cubes 1012, which contain a dichroic mirror passing certain wavelengths and reflecting others. As shown at 1024, the filter cubes 1012 reflect desired wavelengths of the excitation light through one of the objectives as shown at 1026 to the stage 1008. The objectives can have any magnification, but a typical magnification is between 63× and 100×. The excitation light causes the nanoparticles on the sample 1016 to fluoresce, which produces an emission light. The emission light passes through the objective 1010, into the filter cubes 1012, and to the camera 1006. The emission light is at a second wavelength, different than the excitation light, and the filter cubes 1012 are designed to pass light at the second wavelength to the camera 1006. The camera 1006 captures an image of the excitation light in response to a control signal from the computer 1004. The stage 1008 can then be controlled by the computer 1004 to position the sample at a new X-Y-Z position and the process is repeated.

In some embodiments, the above described methods and processes may be tied to a computing system, including one or more computers. In particular, the methods and processes described herein may be implemented as a computer application, computer service, computer API, computer library, and/or other computer program product.

FIG. 11 schematically shows a non-limiting computing device 1100 that may perform one or more of the above described methods and processes. For example, computing device 1100 may represent computer 1004 or aspects of system 1000 described above. Computing device 1100 is shown in simplified form. It is to be understood that virtually any computer architecture may be used without departing from the scope of this disclosure. In different embodiments, computing device 1100 may take the form of a microcomputer, an integrated computer circuit, microchip, a mainframe computer, server computer, desktop computer, laptop computer, tablet computer, home entertainment computer, network computing device, mobile computing device, mobile communication device, gaming device, etc.

Computing device 1100 includes a logic subsystem 1102 and a data-holding subsystem 1104. Computing device 1100 may optionally include a display subsystem 1106, a communication subsystem 1108, an imaging subsystem 1110 and/or other components not shown in FIG. 11. Computing device 1100 may also optionally include user input devices such as manually actuated buttons, switches, keyboards, mice, game controllers, cameras, microphones, and/or touch screens, for example.

Logic subsystem 1102 may include one or more physical devices configured to execute one or more machine-readable instructions. For example, the logic subsystem may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem may include one or more processors that are configured to execute software instructions. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Data-holding subsystem 1104 may include one or more physical, non-transitory, devices configured to hold data and/or instructions executable by the logic subsystem to implement the herein described methods and processes. When such methods and processes are implemented, the state of data-holding subsystem 1104 may be transformed (e.g., to hold different data).

Data-holding subsystem 1104 may include removable media and/or built-in devices. Data-holding subsystem 1104 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1104 may include devices with one or more of the following characteristics: volatile, nonvolatile, dynamic, static, read/write, read-only, random access, sequential access, location addressable, file addressable, and content addressable. In some embodiments, logic subsystem 1102 and data-holding subsystem 1104 may be integrated into one or more common devices, such as an application specific integrated circuit or a system on a chip.

FIG. 11 also shows an aspect of the data-holding subsystem in the form of removable computer-readable storage media 1112, which may be used to store and/or transfer data and/or instructions executable to implement the herein described methods and processes. Removable computer-readable storage media 1112 may take the form of CDs, DVDs, HD-DVDs, Blu-Ray Discs, EEPROMs, flash memory cards, and/or floppy disks, among others.

When included, display subsystem 1106 may be used to present a visual representation of data held by data-holding subsystem 1104. As the herein described methods and processes change the data held by the data-holding subsystem, and thus transform the state of the data-holding subsystem, the state of display subsystem 1106 may likewise be transformed to visually represent changes in the underlying data. Display subsystem 1106 may include one or more display devices utilizing virtually any type of technology. Such display devices may be combined with logic subsystem 1102 and/or data-holding subsystem 1104 in a shared enclosure, or such display devices may be peripheral display devices.

When included, communication subsystem 1108 may be configured to communicatively couple computing device 1100 with one or more other computing devices. Communication subsystem 1108 may include wired and/or wireless communication devices compatible with one or more different communication protocols. As non-limiting examples, the communication subsystem may be configured for communication via a wireless telephone network, a wireless local area network, a wired local area network, a wireless wide area network, a wired wide area network, etc. In some embodiments, the communication subsystem may allow computing device 1100 to send and/or receive messages to and/or from other devices via a network such as the Internet.

When included, imaging subsystem 1110 may be used acquire and/or process any suitable image data from various sensors or imaging devices in communication with computing device 1100. For example, imaging subsystem 1110 may be configured to acquire nanoparticle image data as part of a nanoparticle imaging system, e.g., the SC-QDP platform described above with regard to FIG. 1 or system 1000 described above. Imaging subsystem 1110 may be combined with logic subsystem 1102 and/or data-holding subsystem 1104 in a shared enclosure, or such imaging subsystems may comprise periphery imaging devices. Data received from the imaging subsystem may be held by data-holding subsystem 1104.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

REFERENCES

The following numbered references are cited throughout this disclosure by inclusion of the number reference(s) in square brackets. Each of the following references is hereby incorporated by reference in its entirety.

1. Delom, F. & Chevet, E. Phosphoprotein analysis: from proteins to proteomes. Proteome Sci 4, 15 (2006).
2. Scheele, J. S., Rhee, J. M. & Boss, G. R. Determination of absolute amounts of GDP and GTP bound to Ras in mammalian cells: comparison of parental and Ras-overproducing NIH 3T3 fibroblasts. Proc Natl Acad Sci USA 92, 1097-1100 (1995).
3. Paradela, A. & Albar, J. P. Advances in the Analysis of Protein Phosphorylation. Journal of proteome research 7, 1809-1818 (2008).
4. Hunter, T. Protein kinases and phosphatases: the yin and yang of protein phosphorylation and signaling. Cell 80, 225-236 (1995).
5. Druker, B. J. et al. Five-year follow-up of patients receiving imatinib for chronic myeloid leukemia. N Engl J Med 355, 2408-2417 (2006).
6. Chahrour, O., Cairns, D. & Omran, Z. Small molecule kinase inhibitors as anti-cancer therapeutics. Mini Rev Med Chem 12, 399-411 (2012).
7. Zhang, J., Yang, P. L. & Gray, N. S. Targeting cancer with small molecule kinase inhibitors. Nat Rev Cancer 9, 28-39 (2009).
8. O'Hare, T., Zabriskie, M. S., Eiring, A. M. & Deininger, M. W. Pushing the limits of targeted therapy in chronic myeloid leukaemia. Nat Rev Cancer 12, 513-526 (2012).
9. Dancey, J. & Sausville, E. A. Issues and progress with protein kinase inhibitors for cancer treatment. Nat Rev Drug Discov 2, 296-313 (2003).
10. Hamilton, A. et al. Chronic myeloid leukemia stem cells are not dependent on Bcr-Abl kinase activity for their survival. Blood 119, 1501-1510 (2012).
11. Niepel, M., Spencer, S. L. & Sorger, P. K. Non-genetic cell-to-cell variability and the consequences for pharmacology. Curr Opin Chem Biol 13, 556-561 (2009).
12. Corbin, A. S. et al. Human chronic myeloid leukemia stem cells are insensitive to imatinib despite inhibition of BCR-ABL activity. Journal of Clinical Investigation 121, 396-409 (2011).
13. Fallahi-Sichani, M., Honarnejad, S., Heiser, L. M., Gray, J. W. & Sorger, P. K. Metrics other than potency reveal systematic variation in responses to cancer drugs. Nat Chem Biol 9, 708-714 (2013).
14. Clarke, M. F. et al. Cancer Stem Cells—Perspectives on Current Status and Future Directions: AACR Workshop on Cancer Stem Cells. Cancer Research 66, 9339-9344 (2006).
15. Huntly, B. J. & Gilliland, D. G. Leukaemia stem cells and the evolution of cancer-stem-cell research. Nat Rev Cancer 5, 311-321 (2005).
16. Reya, T., Morrison, S. J., Clarke, M. F. & Weissman, I. L. Stem cells, cancer, and cancer stem cells. Nature 414, 105-111 (2001).
17. Crews, L. A. & Jamieson, C. H. Chronic myeloid leukemia stem cell biology. Curr Hematol Malig Rep 7, 125-132 (2012).
18. Bhatia, R. et al. Persistence of malignant hematopoietic progenitors in chronic myelogenous leukemia patients in complete cytogenetic remission following imatinib mesylate treatment. Blood 101, 4701-4707 (2003).
19. Chu, S. et al. Persistence of leukemia stem cells in chronic myelogenous leukemia patients in prolonged remission with imatinib treatment. Blood 118, 5565-5572 (2011).
20. Krutzik, P. O., Trejo, A., Schulz, K. R. & Nolan, G. P. Phospho flow cytometry methods for the analysis of 21. Hamilton, A. et al. BCR-ABL activity and its response to drugs can be determined in CD34+ CML stem cells by CrkL phosphorylation status using flow cytometry. Leukemia 20, 1035-1039 (2006).
22. Schulz, K. R., Danna, E. A., Krutzik, P. O. & Nolan, G. P. Single-cell phospho-protein analysis by flow cytometry. Curr Protoc Immunol Chapter 8, Unit 8.17.11-20 (2012).
23. Warsch, W. et al. High STAT5 levels mediate imatinib resistance and indicate disease progression in chronic myeloid leukemia. Blood 117, 3409-3420 (2011).
24. Hantschel, O. et al. BCR-ABL uncouples canonical JAK2-STAT5 signaling in chronic myeloid leukemia. Nat Chem Biol 8, 285-293 (2012).
25. Hughes, T. P. et al. Frequency of major molecular responses to imatinib or interferon alfa plus cytarabine in newly diagnosed chronic myeloid leukemia. N Engl J Med 349, 1423-1432 (2003).
26. Merante, S. et al. Outcome of four patients with chronic myeloid leukemia after imatinib mesylate discontinuation. Haematologica 90, 979-981 (2005).
27. Rousselot, P. et al. Imatinib mesylate discontinuation in patients with chronic myelogenous leukemia in complete molecular remission for more than 2 years. Blood 109, 58-60 (2007).
28. Phillips, R. M., Bair, E., Lawrence, D. S., Sims, C. E. & Allbritton, N. L. Measurement of protein tyrosine phosphatase activity in single cells by capillary electrophoresis. Anal Chem 85, 6136-6142 (2013).
29. Dovichi, N. J. & Hu, S. Chemical cytometry. Current Opinion in Chemical Biology 7, 603-608 (2003).
30. Bendall, S. C. et al. Single-Cell Mass Cytometry of Differential Immune and Drug Responses Across a Human Hematopoietic Continuum. Science 332, 687-696 (2011).
31. Edelstein, A., Amodaj, N., Hoover, K., Vale, R. & Stuurman, N. Computer control of microscopes using microManager. Curr Protoc Mol Biol Chapter 14, Unit 14.20 (2010).
32. Carpenter, A. E. et al. CellProfiler: image analysis software for identifying and quantifying cell phenotypes. Genome Biol 7, R100 (2006).
33. Parthasarathy, R. Rapid, accurate particle tracking by calculation of radial symmetry centers. Nat Methods 9, 724-726 (2012).
34. Fichter, K. M., Flajolet, M., Greengard, P. & Vu, T. Q. Kinetics of G-protein-coupled receptor endosomal trafficking pathways revealed by single quantum dots. Proc Natl Acad Sci USA 107, 18658-18663 (2010).
35. Scholl, B. et al. Single Particle Quantum Dot Imaging Achieves Ultrasensitive Detection Capabilities for Western Immunoblot Analysis. ACS Nano 3, 1318-1328 (2009).
36. Scott, D. W. On optimal and data-based histograms. Biometrika 66, 605-610 (1979).
37. Parzen, E. On Estimation of a Probability Density Function and Mode. Ann. Math. Statist. 33, 1065-1076 (1962).
38. Wahba, G. Optimal Convergence Properties of Variable Knot, Kernel, and Orthogonal Series Methods for Density Estimation. The Annals of Statistics 3, 15-29 (1975).
39. Silverman, B. W. Density Estimation for Statistics and Data Analysis. CRC Press (1986).

The invention claimed is:

1. A computer-implemented method of quantifying the activity level of a target biomolecule in a sample comprising one or more intact cells, said sample having been treated with a reagent, said reagent comprising a label that can label a cellular structure such that the label can be localized within a cell, and a binding component that binds the target biomolecule, said target biomolecule exhibiting a first activity level within the cell and a second activity level within the sample:
   receiving a set of images of the sample, wherein the images within the set comprise individual cells and are taken at a plurality of depths;
   detecting a first cell in the images of the sample at the plurality of depths;
   detecting and localizing the label at individual sites in the first cell at each depth in the plurality of depths comprising applying a spatial band-pass filter, detecting localized maxima, and calculating a position of each label in the cell at each depth in the plurality of depths, wherein detecting localized maxima is performed using centroid localization or radial symmetry localization;
   calculating a total number of detected and localized labels within the first cell; and
   calculating a first activity level of the target biomolecule within the cell based on the total number of detected and localized labels at individual sites in the cell;
   calculating the first activity level of the target biomolecule within a plurality of cells in the sample; and
   calculating the activity level of the target biomolecule within the sample based on the number of detected and localized labels in the plurality of cells.

2. The method of claim 1, further comprising calculating a continuous probability density function of the first activity level in a subset of cells in the sample based on the total number of detected and localized labels in each cell.

3. The method of claim 2, wherein the second activity level of the target biomolecule is calculated based on the continuous probability density function of the first activity level of a plurality cells in the sample based on the total number of detected and localized labels in each cell in the plurality of cells.

4. The method of claim 2, wherein the continuous probability density functions is calculated using a Gaussian kernel density estimation.

5. The method of claim 1, wherein the target biomolecule is a protein that is modified by phosphorylation and the activity of the target biomolecule comprises phosphorylation.

6. The method of claim 1, wherein the label comprises a quantum dot and the images comprise fluorescent micrographs.

7. The method of claim 1, wherein detecting the first cell comprises detecting a nucleus and plasma membrane of the first cell via a threshold-based intensity algorithm and a membrane expansion cell segmentation algorithm.

8. The method of claim 1, wherein the binding component comprises an antibody or antigen binding fragment thereof or a nucleic acid molecule.

9. The method of claim 1, wherein the images of the sample at the plurality of depths comprise z-stacks at multiple fields of view of the sample.

10. The method of claim 1, wherein calculating the total number of detected and localized labels in each cell comprises summing pixel values corresponding to the first cell from all depths in the plurality of depths and subtracting a global approach value for each field of view.

11. A computer-implemented method of quantifying the activity level of a target biomolecule in a sample comprising one or more intact cells, said sample having been treated with a reagent, said reagent comprising a label that can label a cellular structure such that the label can be localized within a cell, and a binding component that binds the target biomolecule, said target biomolecule exhibiting a first activity level within the cell and a second activity level within the sample:

receiving a set of images of the sample, wherein the images within the set comprise individual cells and are taken at a plurality of depths, wherein the images of the sample at the plurality of depths comprise z-stacks at multiple fields of view of the sample;

detecting a first cell in the images of the sample at the plurality of depths;

detecting and localizing the label at individual sites in the first cell at each depth in the plurality of depths;

calculating a total number of detected and localized labels within the first cell, comprising summing pixel values corresponding to the first cell from all depths in the plurality of depths and subtracting a global background value for each field of view, wherein the global background value for each field of view is calculated as a mean of a minimum pixel value corresponding to each y-column of the field of view; and calculating a first activity level of the target biomolecule within the cell based on the total number of detected and localized labels at individual sites in the cell;

calculating the first activity level of the target biomolecule within a plurality of cells in the sample; and calculating the activity level of the target biomolecule within the sample based on the number of detected and localized labels in the plurality of cells.

12. The method of claim 11, further comprising calculating a continuous probability density function of the first activity level in a subset of cells in the sample based on the total number of detected and localized labels in each cell.

13. The method of claim 11, wherein the target biomolecule is a protein that is modified by phosphorylation and the activity of the target biomolecule comprises phosphorylation.

14. A method of identifying a change in activity of a target biomolecule in response to a test compound, the method comprising:

treating a first set of cells with a first concentration of the test compound;

treating a second set of cells with a negative control;

contacting the first set of cells and second set of cells with a first reagent, said first reagent comprising a first label that can label a cellular structure such that the label can be localized within the cell, and a first binding component that binds a first target biomolecule;

calculating the activity of the target molecule in the first set of cells and the second set of cells using the steps of:

a) receiving a set of images of the first set of cells and the second set of cells, wherein the images within each set comprise individual cells and are taken at a plurality of depths;

b) detecting a first cell in the images of the first set of cells and a first cell in the images of the second set of cells at the plurality of depths;

c) detecting and localizing the label at individual sites at each depth in the plurality of depths in the first cell in the first set of cells and in the first cell in the second set of cells comprising applying a spatial band-pass filter, detecting localized maxima, and calculating a position of each label in the cell at each depth in the plurality of depths, wherein detecting localized maxima is performed using centroid localization or radial symmetry localization;

d) calculating a total number of detected and localized labels within the first cell in the first set of cells and in the first cell in the second set of cells;

e) calculating a first activity level of the target biomolecule within i) a plurality of cells in the first set of cells and ii) a plurality of cells in the second set of cells;

f) calculating the activity level of the target biomolecule within the first set of cells and the second set of cells based on the number of detected and localized labels in the plurality of cells; and g) comparing the activity level of the target biomolecule within the first set of cells with the activity level of the target biomolecule within the second set of cells.

15. The method of claim 14, wherein the test compound comprises a potential therapeutic compound, a known therapeutic compound, or a combination of two or more known therapeutic compounds.

16. The method of claim 14, further comprising treating a third set of cells with a second concentration of the test compound, contacting the third set of cells with the reagent, and calculating the activity of the target biomolecule in the third set of cells.

17. The method of claim 14, further comprising identifying a population of cells within the first set of cells that is resistant to the test compound at the first concentration of the test compound.

18. The method of claim 14, further comprising contacting the first set of cells and second set of cells within a second reagent, said second reagent comprising a second label that can label a cellular structure such that the label can be localized within the cell and a second binding component that binds a second target biomolecule, and wherein the first label comprises a quantum dot of a first color and the second label comprises a quantum dot of a second color.

19. The method of claim 14, wherein the first set of cells comprises cells derived from a human cancer patient.

* * * * *

UNITED STATES PATENT AND TRADEMARK OFFICE
CERTIFICATE OF CORRECTION

| | | |
|---|---|---|
| PATENT NO. | : 10,083,341 B2 | Page 1 of 1 |
| APPLICATION NO. | : 14/946535 | |
| DATED | : September 25, 2018 | |
| INVENTOR(S) | : Tania Vu and Thomas Jacob | |

It is certified that error appears in the above-identified patent and that said Letters Patent is hereby corrected as shown below:

At Column 1, Lines 16, please delete the following heading and paragraph:
"ACKNOWLEDGEMENT OF GOVERNMENT SUPPORT
This invention was made with United States government support under the terms of grant number GBMEN0125 awarded by the National Institutes of Health. The United States government has certain rights in this invention."

And replace it with the following heading and paragraph:
-- GOVERNMENT SUPPORT
This invention was made with government support under NS071116 awarded by the National Institutes of Health. The government has certain rights in the invention. --

Signed and Sealed this
Ninth Day of July, 2019

Andrei Iancu
*Director of the United States Patent and Trademark Office*